US011542477B2

(12) United States Patent
Park et al.

(10) Patent No.: US 11,542,477 B2
(45) Date of Patent: Jan. 3, 2023

(54) **VIRUS-LIKE PARTICLES CO-EXPRESSING *TOXOPLASMA GONDII* IMC, ROP18, AND MIC8, AND PHARMACEUTICAL COMPOSITION COMPRISING THE SAME**

(71) Applicant: Health Park Co., Ltd., Seoul (KR)

(72) Inventors: Hyunwoo Park, Seoul (KR); Hui Jin, Seoul (KR); Fu Shi Quan, Seoul (KR)

(73) Assignee: Health Park Co., Ltd., Seoul (KR)

( * ) Notice: Subject to any disclaimer, the term of this patent is extended or adjusted under 35 U.S.C. 154(b) by 122 days.

(21) Appl. No.: 16/901,705

(22) Filed: Jun. 15, 2020

(65) Prior Publication Data

US 2021/0207102 A1 Jul. 8, 2021

(30) Foreign Application Priority Data

Jan. 7, 2020 (KR) ........................ 10-2020-0001828

(51) Int. Cl.

| | |
|---|---|
| ***C12N 7/00*** | (2006.01) |
| ***A61P 33/02*** | (2006.01) |
| ***A61K 9/00*** | (2006.01) |
| ***A61K 31/7084*** | (2006.01) |
| ***A61K 39/145*** | (2006.01) |
| ***C07K 14/005*** | (2006.01) |
| ***C07K 14/45*** | (2006.01) |
| ***C12N 15/86*** | (2006.01) |
| *A61K 39/00* | (2006.01) |

(52) U.S. Cl.

CPC .............. *C12N 7/00* (2013.01); *A61K 9/0043* (2013.01); *A61K 31/7084* (2013.01); *A61K 39/145* (2013.01); *A61P 33/02* (2018.01); *C07K 14/005* (2013.01); *C07K 14/45* (2013.01); *C12N 15/86* (2013.01); *A61K 2039/5258* (2013.01); *A61K 2039/543* (2013.01); *C12N 2710/14043* (2013.01); *C12N 2760/16022* (2013.01); *C12N 2760/16023* (2013.01); *C12N 2760/16052* (2013.01)

(58) Field of Classification Search

None

See application file for complete search history.

(56) References Cited

PUBLICATIONS

Kang, S.M., et al., “Virus-like particles as universal influenza vaccines”, Expert Rev. Vaccines, Aug. 2012; 11(8):995-1007.

Kushnir, N., et al., “Virus-like particles as a highly efficient vaccine platform: Diversity of targets and production systems and advances in clinical development”, Vaccine 31 (2012) 58-83.

Lee, S.H., et al., “Protective Immunity Induced by Incorporating Multiple Antigenic Proteins of Toxoplasma gondii into Influenza-Virus Like Particles”, Frontiers in Immunology, vol. 9, Article 3073, 9 pages, Jan. 2019.

Lee, S.H., et al., “Virus-like particles containing multiple antigenic proteins of Toxoplasma gondii induce memory T cell and B cell responses”, PLoS One 14(8): e0220865, Aug. 2019.

Roldão, A., et al., “Virus-like particles in vaccine development”, Expert Rev. Vaccines 9(10), 2010, 1149-1176.

*Primary Examiner* — Benjamin P Blumel

(74) *Attorney, Agent, or Firm* — Hamilton, Brook, Smith & Reynolds, P.C.

(57) ABSTRACT

The present invention relates to a virus-like particle for preventing or treating toxoplasmosis, comprising influenza virus matrix protein 1; and surface antigen proteins comprising an inner membrane complex, Rhoptry protein 18 and Microneme protein 8 derived from *Toxoplasma gondii*, and a pharmaceutical composition comprising the same.

13 Claims, 16 Drawing Sheets

Specification includes a Sequence Listing.

FIG. 6
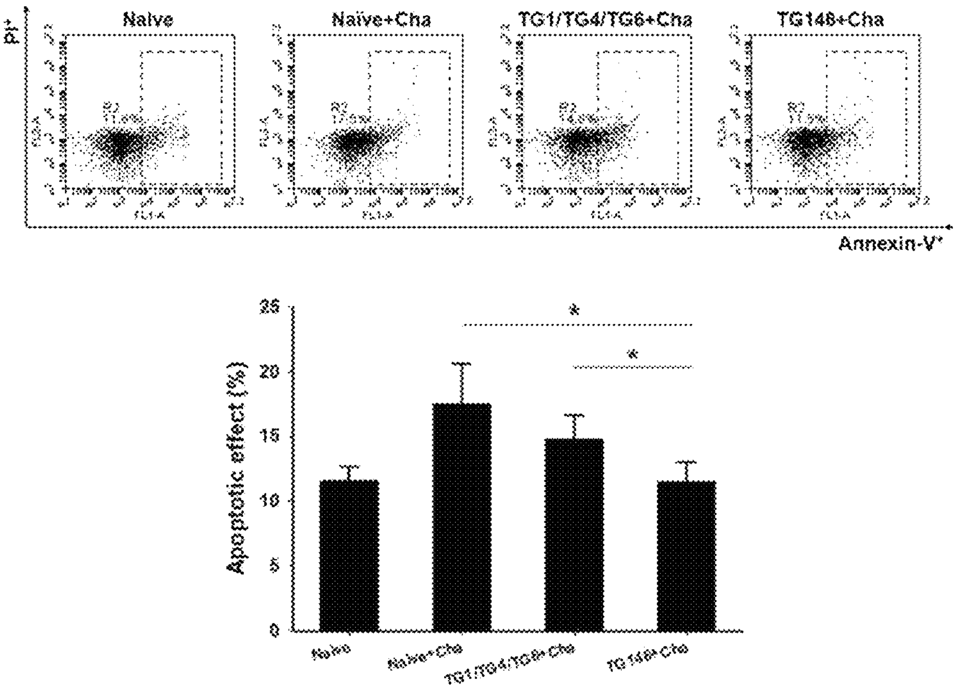
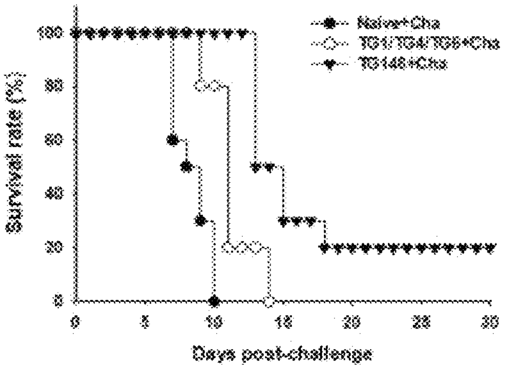
FIG. 7A
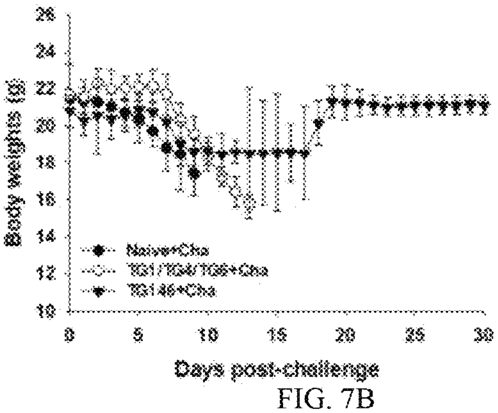
FIG. 7B
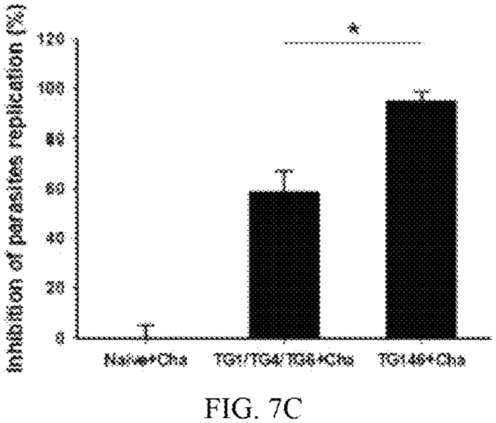
FIG. 7C

<Group> (n=6)
1. Naïve
2. TG146 VLPs (IM)
3. TG146 VLPs (IN)
4. TG146 VLPs + CpG (IM)
5. TG146 VLPs + CpG (IN)
6. Naïve + cha Immunization route : Intramuscular and Intranasal Challenge infection : *T.gondii* ME49 450 cyst Challenge route : oral

SEQUENCE LISTING

```
<160> NUMBER OF SEQ ID NOS: 8

<210> SEQ ID NO 1
<211> LENGTH: 252
<212> TYPE: PRT
<213> ORGANISM: Influenza virus

<400> SEQUENCE: 1

Met Ser Leu Leu Thr Glu Val Glu Thr Tyr Val Leu Ser Ile Ile Pro
1               5                   10                  15
```

-continued

```
Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 2
<211> LENGTH: 164
<212> TYPE: PRT
<213> ORGANISM: Toxoplasma gondii

<400> SEQUENCE: 2

```
Met Gly Asn Thr Ala Cys Cys Gly Phe Asp Ser Asp Ser Thr Ala Asp
1               5                   10                  15

Leu Glu Ile Gly Arg Glu Gly Glu Val Arg Ser Arg Lys Pro Ile Gln
            20                  25                  30

Val Ser Lys Glu Ala Phe Asp Asn Trp Met Asn Arg Tyr Glu Ala Gly
        35                  40                  45

Asp Thr Met Glu Val Leu Phe Pro Asp Gly His Arg Ile Glu Cys Asn
    50                  55                  60

Leu Lys Ile Asp Arg Pro Lys Asn Phe Met Asn Leu Thr Phe Asn Gln
65                  70                  75                  80

Lys Val Arg Pro Ile Gln Leu Asp Asp Ile Ala Ala Val Leu Tyr Gly
                85                  90                  95

Ser Asp Pro Arg Ser Ser Glu Cys Ala Asp Ser Lys Met Leu Arg Asn
            100                 105                 110

Pro Cys Val Val Gly Phe Arg Leu Ala Ser Ser Gly Arg Ala Ile Ala
        115                 120                 125

Phe Ser Phe Lys Asp Ile Thr Asp Ala Gln Cys Phe Val Ser Phe Leu
    130                 135                 140
```

```
Asp Asp Glu Ile Lys Lys Asn Gln Glu Ser Asn Lys Ser Ser Ala Ser
145                 150                 155                 160

Asn Asp Arg Asn


<210> SEQ ID NO 3
<211> LENGTH: 554
<212> TYPE: PRT
<213> ORGANISM: Toxoplasma gondii

<400> SEQUENCE: 3

Met Phe Ser Val Gln Arg Pro Pro Leu Thr Arg Thr Val Val Arg Met
1               5                   10                  15

Gly Leu Ala Thr Leu Leu Pro Lys Thr Ala Cys Leu Ala Gly Leu Asn
            20                  25                  30

Val Ala Leu Val Phe Leu Leu Phe Gln Val Gln Asp Gly Thr Gly Ile
        35                  40                  45

Thr Leu Gly Pro Ser Lys Leu Asp Ser Lys Pro Thr Ser Leu Asp Ser
    50                  55                  60

Gln Gln His Val Ala Asp Lys Arg Trp Leu Ala Thr Val Gly His Tyr
65                  70                  75                  80

Lys His Leu Ala Gly Ala Thr Glu Ser Thr Arg Asp Val Ser Leu Leu
                85                  90                  95

Glu Glu Arg Ala Gln His Arg Val Asn Ala Gln Glu Thr Asn Gln Arg
            100                 105                 110

Arg Thr Ile Phe Gln Arg Leu Leu Asn Leu Leu Arg Arg Glu Arg
        115                 120                 125

Asp Gly Glu Val Ser Gly Ser Ala Ala Asp Ser Ser Ser Arg Pro Arg
    130                 135                 140

Leu Ser Val Arg Gln Arg Leu Ala Gln Leu Trp Arg Arg Ala Lys Ser
145                 150                 155                 160

Leu Phe Lys Arg Gly Ile Arg Arg Tyr Phe Pro Gln Gly Arg Asn Arg
                165                 170                 175

Gln Arg Ser Leu Arg Ala Gln Arg Arg Arg Ser Glu Leu Val Phe Glu
            180                 185                 190

Lys Ala Asp Ser Gly Cys Val Ile Gly Lys Arg Ile Leu Ala His Met
        195                 200                 205

Gln Glu Gln Ile Gly Gln Pro Gln Ala Leu Glu Asn Ser Glu Arg Leu
    210                 215                 220

Asp Arg Ile Leu Thr Val Ala Ala Trp Pro Pro Asp Val Pro Lys Arg
225                 230                 235                 240

Phe Val Ser Val Thr Thr Gly Glu Thr Arg Thr Leu Val Arg Gly Ala
                245                 250                 255

Pro Leu Gly Ser Gly Gly Phe Ala Thr Val Tyr Glu Ala Thr Asp Val
            260                 265                 270

Glu Thr Asn Glu Glu Leu Ala Val Lys Val Phe Met Ser Glu Lys Glu
        275                 280                 285

Pro Thr Asp Glu Thr Met Leu Asp Leu Gln Arg Glu Ser Ser Cys Tyr
    290                 295                 300

Arg Asn Phe Ser Leu Ala Lys Thr Ala Lys Asp Ala Gln Glu Ser Cys
305                 310                 315                 320

Arg Phe Met Val Pro Ser Asp Val Val Met Leu Glu Gly Gln Pro Ala
                325                 330                 335

Ser Thr Glu Val Val Ile Gly Leu Thr Thr Arg Trp Val Pro Asn Tyr
            340                 345                 350
```

-continued

```
Phe Leu Leu Met Met Arg Ala Glu Ala Asp Met Ser Lys Val Ile Ser
        355                 360                 365

Trp Val Phe Gly Asp Ala Ser Val Asn Lys Ser Glu Phe Gly Leu Val
    370                 375                 380

Val Arg Met Tyr Leu Ser Ser Gln Ala Ile Lys Leu Val Ala Asn Val
385                 390                 395                 400

Gln Ala Gln Gly Ile Val His Thr Asp Ile Lys Pro Ala Asn Phe Leu
                405                 410                 415

Leu Leu Lys Asp Gly Arg Leu Phe Leu Gly Asp Phe Gly Thr Tyr Arg
            420                 425                 430

Ile Asn Asn Ser Val Gly Arg Ala Ile Gly Thr Pro Gly Tyr Glu Pro
        435                 440                 445

Pro Glu Arg Pro Phe Gln Ala Thr Gly Ile Thr Tyr Thr Phe Pro Thr
    450                 455                 460

Asp Ala Trp Gln Leu Gly Ile Thr Leu Tyr Cys Ile Trp Cys Lys Glu
465                 470                 475                 480

Arg Pro Thr Pro Ala Asp Gly Ile Trp Asp Tyr Leu His Phe Ala Asp
                485                 490                 495

Cys Pro Ser Thr Pro Glu Leu Val Gln Asp Leu Ile Arg Ser Leu Leu
            500                 505                 510

Asn Arg Asp Pro Gln Lys Arg Met Leu Pro Leu Gln Ala Leu Glu Thr
        515                 520                 525

Ala Ala Phe Lys Glu Met Asp Ser Val Val Lys Gly Ala Ala Gln Asn
    530                 535                 540

Phe Glu Gln Gln Glu His Leu His Thr Glu
545                 550


<210> SEQ ID NO 4
<211> LENGTH: 684
<212> TYPE: PRT
<213> ORGANISM: Toxoplasma gondii

<400> SEQUENCE: 4

Met Lys Ala Asn Arg Ile Trp Cys Phe Phe Ala Trp Arg Met Val Val
1               5                   10                  15

Arg Ala Ser Phe Leu Lys Glu Met Asp Ser Ile Phe Val Ser Ala Ile
            20                  25                  30

Arg Gln Asn Val Gln His Thr His Ser Ala Leu Leu Ala Lys Leu Lys
        35                  40                  45

Glu Pro Pro Asp Pro Asp Asp Glu Asn Ser Trp Leu Cys Arg Ile Ser
    50                  55                  60

Lys Lys Tyr Asp Ala Cys Gly Ser Arg Glu Tyr Ser Asp Lys Gly Leu
65                  70                  75                  80

Lys Gly Thr Tyr Cys Pro Glu Asp Phe Cys Cys Ser Lys Thr Ala Cys
                85                  90                  95

Phe Tyr Gly Ser Cys Gly Ser Trp Cys His Asp Asn Trp Ala Leu Cys
            100                 105                 110

Ser Ser Ser Ile Ile Tyr His Asp Glu Tyr Ser Tyr Gly Lys Cys Asn
        115                 120                 125

Cys Lys Arg Phe Gln Glu Asn Cys Asp Val Asn Ala Ile Cys Val His
    130                 135                 140

Ala Asn Arg Glu Asp Gly Gly Ala Tyr Cys Gln Cys Lys Glu Gly Tyr
145                 150                 155                 160

Trp Gly Asp Gly Lys Ser Cys Lys Ile Asp Phe Cys Gln Leu Gln Pro
```

-continued

```
                165                 170                 175

Cys Gly Ala Gly Thr Cys Thr Arg Thr Asp Glu Gly Tyr Lys Cys Asp
            180                 185                 190

Cys Pro Glu Thr His Lys Leu Ile Val Val Glu Asp Lys Glu Thr Cys
        195                 200                 205

Lys Ala Lys Pro Asp Phe Cys Ala Glu Glu Pro Cys Gly Pro Pro Ser
    210                 215                 220

Met Val Glu Asn Cys Val Asn Thr Asp Asp Ser Tyr Glu Cys Val Cys
225                 230                 235                 240

Lys Gln Gly Tyr Glu Val Arg Asn Gly Arg Cys Glu Glu Ile Asp Leu
                245                 250                 255

Cys Ala Asp Lys Pro Cys Gly Pro Asp Glu Gly Val His Glu Cys Val
            260                 265                 270

Thr Glu Arg Gln Pro Lys Leu Arg Tyr Arg Cys Thr Cys Lys Ala Gly
        275                 280                 285

Phe Asp Leu Thr Thr Leu Pro Asp Gly Val Ser Gln Lys Cys Leu Lys
    290                 295                 300

Asn Phe Cys Tyr Glu Glu Pro Cys Gly Thr Arg Asp Leu Val Glu Ser
305                 310                 315                 320

Cys Lys Ser Lys Ala Tyr Gly Tyr Ser Cys Leu Cys Ala Ala Gly Ala
                325                 330                 335

Met Val Gln Val Ile Asn Gly Lys Glu Lys Cys Ile Lys Ala Asp Leu
            340                 345                 350

Cys Arg Asn Asp Pro Cys Gly Pro Glu Thr Ala Val Ile Gln Cys Tyr
        355                 360                 365

Ser His Gly Thr Ser Tyr Arg Cys Leu Cys Lys Ala Gly Tyr Thr Glu
    370                 375                 380

Val Phe Val Asn Gly Lys Ser Ser Cys Gln Lys Gly Asp Pro Cys Thr
385                 390                 395                 400

Leu Asn Met Cys Gly Gly Asn Glu Ala Val Gln Glu Cys Thr Thr Asp
                405                 410                 415

Gly Thr Ala Tyr Gly Cys Thr Cys Lys Pro Gly Tyr Ser Ile Ala Ile
            420                 425                 430

Lys His Gly Gln Lys Phe Cys Asn Pro Glu Glu Glu Cys Ala Ser His
        435                 440                 445

Cys Gly Ser Ala Ala Ala Val Lys Ser Cys Glu Ile Leu Asp Ser Gly
    450                 455                 460

Gly Tyr Gln Cys Thr Cys Asn Pro Gly Tyr Val Met Arg Tyr Ser Asp
465                 470                 475                 480

Tyr Val Lys Gly Cys Val Glu Gly Asn Gln Cys Ser Leu Asn Pro Cys
                485                 490                 495

Gly Glu Gln Glu Ala Val Gln Arg Cys Ile Pro Glu Gly Asp Thr Tyr
            500                 505                 510

Asp Cys Glu Cys Asn Pro Gly Phe Val Lys Arg Val Leu Pro Asp Gly
        515                 520                 525

Asn Phe Ile Cys Ala Asp Pro Ala Ser Cys Val Gly Asn Pro Cys Gly
    530                 535                 540

Ser Ser Asp Ala Val Asp Ala Cys Ile Ala Gly Thr Ser Thr Tyr Thr
545                 550                 555                 560

Cys Arg Cys Lys Asp Gly Tyr Thr Pro Gln Ser Ile Gly Ser Lys Leu
                565                 570                 575

Gln Cys Leu Pro Glu Ser Thr Asp Gln Thr Asp Phe Asp Ser Lys His
            580                 585                 590
```

```
Lys Pro Glu Asp Asn Lys Gly Arg Tyr Ser Lys Gly Thr Ile Ala Leu
        595                 600                 605

Val Val Val Gly Cys Val Ala Leu Leu Gly Ile Ile Ala Gly Gly Ile
    610                 615                 620

Ser Tyr Ala Arg Asn Arg Gly Gly Glu Arg Asp Asp Glu Asp Leu Ala
625                 630                 635                 640

Pro Pro Pro Arg Ser Thr Arg Glu Arg Arg Leu Ser Ser Met Gly Glu
                645                 650                 655

Gly Phe Glu Asn Ala Ser Trp Ala Ser Ser Val Ser Met Ile Pro Ser
            660                 665                 670

Ala Pro Ala Pro Pro Pro Ser Gly Gly Ile Trp Ser
        675                 680


<210> SEQ ID NO 5
<211> LENGTH: 1027
<212> TYPE: DNA
<213> ORGANISM: Influenza virus

<400> SEQUENCE: 5

agcgaaagca ggtagatatt gaaagatgag tcttctaacc gaggtcgaaa cgtacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttggaactca tcctagctcc agtgctggtc tgaaaaatga    720

tcttcttgaa aatttgcagg cctatcagaa acgaatgggg gtgcagatgc aacggttcaa    780

gtgatcctct cactattgcc gcaaatatca ttgggatctt gcacttgaca ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027


<210> SEQ ID NO 6
<211> LENGTH: 495
<212> TYPE: DNA
<213> ORGANISM: Toxoplasma gondii

<400> SEQUENCE: 6

atggggaaca cggcgtgctg cggtttcgac agtgactcta ctgctgacct cgagatcggt     60

cgagaggggg aagtgcggag tcgcaaacca attcaggtat ccaaagaggc gtttgacaac    120

tggatgaatc gttatgaggc cggagacacg atggaagtgc tttttcctga tggtcaccga    180

attgagtgta acttgaaaat cgaccgaccg aaaaacttca tgaatctcac cttcaatcag    240
```

-continued

```
aaagtaagac ccatccagct ggatgacatt gcagctgtcc tatatggctc ggatcctcgc    300

agttccgaat gcgcagatag caaaatgctg cgaaacccct gtgtcgtggg cttccgcctc    360

gcgagctctg gacgagccat cgcgttttct tttaaagaca tcacggacgc gcagtgtttt    420

gtgtctttcc tggacgacga aatcaagaag aatcaggagt caaacaagtc ttcagcaagc    480

aacgacagaa actaa                                                     495


<210> SEQ ID NO 7
<211> LENGTH: 1665
<212> TYPE: DNA
<213> ORGANISM: Toxoplasma gondii

<400> SEQUENCE: 7

atgttttcgg tacagcggcc acctcttacg cgtaccgtcg tccgaatggg tttagcgact     60

cttctcccga agacagcctg tcttgcgggg ttaaatgtag cgcttgtctt cctgctcttc    120

caagtccagg atgggaccgg aatcacactt ggtccttcaa aactcgactc caaaccgaca    180

agtttggatt cgcaacagca cgttgctgac aagcggtggc ttgctacagt tggccactac    240

aaacatttag caggagcgac agaaagcact cgagacgttt cattgctgga ggaaagggct    300

caacaccggg taaatgcgca agaaacaaac caacggcgca cgatttttca gaggcttctg    360

aatctcttga gacggagaga aagagatggt gaagtctcgg gttccgcagc tgatagctcc    420

tcgagacccc gtctgtccgt acgacagagg cttgctcaac tttggcgtag agcgaaatcg    480

ttattcaaac gcggaatccg gaggtacttt cctcaagggc gtaaccgaca gcgaagtttg    540

cgggcacaaa gacggcgatc tgaattggtt tttgagaagg cggattctgg atgcgtcatc    600

ggcaaacgca tcctggcgca catgcaagaa caaatcgggc agcctcaagc gctagaaaat    660

agtgaacgac tggatagaat tctgactgtc gccgcctggc ctccggacgt tccaaaaaga    720

tttgtttctg tgactaccgg tgaaacccgg acgctggtga gaggtgcacc ccttggctct    780

ggtggattcg ccactgtata tgaggctaca gacgtggaga cgaatgaaga gttggctgtt    840

aaggttttca tgtcagaaaa ggagcccacc gatgagacta tgcttgactt gcagagggag    900

tcgtcctgct acaggaactt tagtctagcc aagacggcga aggatgccca ggaaagctgt    960

agattcatgg ttcctagtga tgttgtgatg ttagagggac agccagcatc cacagaggtc   1020

gtgattggtt tgacgactcg gtgggtacca aactattttc ttctcatgat gcgggcagaa   1080

gcggacatga gcaaagtcat ttcatgggta tttggagatg cgtctgtcaa taaaagtgaa   1140

tttggcctgg tcgttcgaat gtacctatcc agtcaggcaa tcaaactagt ggccaatgtt   1200

caagctcagg gaattgtgca tacggatatc aaaccggcga atttcctcct cttgaaagac   1260

ggtcgcctgt ttctcggcga cttcggaacg tatagaatca ataattcggt tggacgcgcg   1320

ataggtactc ccggttacga gcctccggag cgaccgtttc aggctacagg catcacctat   1380

acattcccca ctgacgcgtg gcaactcggt ataactttgt actgcatctg gtgcaaggaa   1440

cgtccaactc cggccgacgg catctgggac tacttacact tcgcagattg tccttccacg   1500

cctgagctgg ttcaagacct catccgaagc ctcttgaatc gagatcctca gaaacggatg   1560

ctcccgctac aagccttgga gacagcagcg tttaaagaga tggattcagt agtaaaaggc   1620

gccgcgcaaa acttcgaaca gcaggaacat ctccacacag aataa                   1665


<210> SEQ ID NO 8
<211> LENGTH: 2055
<212> TYPE: DNA
<213> ORGANISM: Toxoplasma gondii
```

-continued

<400> SEQUENCE: 8

```
atgaaggcca atcgaatatg gtgttttttt gcgtggcgta tggttgtgcg ggcctcattt     60
ctgaaagaga tggacagcat tttcgtttct gctatccgac agaatgtaca gcatactcat    120
tctgcccttc tcgccaaact gaaggaaccc ccagatccag atgatgagaa ctcttggctt    180
tgtcgaatat caaaaaaata tgacgcatgc ggtagcaggg aatattccga taagggcctc    240
aaagggacgt actgtcccga ggatttttgc tgtagcaaga cggcatgttt ttacggttca    300
tgtgggagtt ggtgccacga caactgggct ctgtgcagct catctataat ctaccacgac    360
gagtacagtt acgggaaatg caactgtaaa cggtttcaag aaaactgtga tgtgaatgca    420
atttgtgtgc atgcgaacag agaggatggc ggtgcgtatt gtcagtgcaa ggaaggatat    480
tggggtgatg gtaaatcgtg caagattgac ttctgccaac tgcagccctg tggtgcaggg    540
acctgcacca ggacggatga aggatacaag tgtgattgcc cagaaactca caagcttatt    600
gtcgttgaag acaaagagac gtgcaaggca aaaccggact tttgcgcgga agagccttgc    660
ggaccaccct ctatggttga aaattgcgtg aacaccgatg acagctacga atgtgtttgc    720
aaacaggggt atgaagtgag gaacggtcgg tgcgaagaaa ttgacttatg cgcggacaag    780
ccatgtgggc cagatgaggg tgtgcatgag tgtgtaacag agaggcaacc gaaattaagg    840
tacagatgca cgtgcaaggc aggattcgat ttgaccacct tgcctgatgg tgtttcccag    900
aagtgcctga agaacttctg ttacgaggag ccctgcggca cccgggacct agttgaaagc    960
tgtaagtcaa aggcatatgg atactcgtgt ttgtgtgcgg caggtgccat ggttcaagtg   1020
attaacggaa aagaaaagtg catcaaggcg gacttgtgcc gcaatgatcc gtgtggtcca   1080
gagacagcag tgattcaatg ttactctcat ggcaccagct ataggtgttt gtgcaaagca   1140
ggctacactg aagtttttgt taacgggaag agttcatgtc aaaagggcga cccatgcact   1200
ctgaacatgt gtggcggtaa cgaagcggtc caggagtgca caactgatgg cacggcgtac   1260
gggtgtacct gcaagccagg ctattcgata gccattaagc atggtcagaa gttttgcaac   1320
cctgaagagg agtgtgcttc tcattgtggc tcggcagctg cagtgaaaag ctgtgaaata   1380
cttgactctg gcggatacca gtgtacatgc aatccaggat acgtcatgag atacagcgac   1440
tatgtaaaag gatgcgtcga gggaaatcag tgttctctca atccttgtgg ggagcaggaa   1500
gccgtgcaaa ggtgcattcc tgaaggtgac acgtatgatt gcgagtgcaa tccggggttc   1560
gtcaaaagag tcttgccgga tggaatttc atttgcgccg atccagcgag ctgtgtaggg   1620
aatccctgtg gtagctcaga tgcggtcgat gcgtgcattg ccgggactag cacgtataca   1680
tgcaggtgta aggacggata cacacctcag tcaattgggt caaagttgca gtgtttacca   1740
gaaagcactg atcagacaga tttcgattcc aaacacaaac cagaggacaa caaaggtcga   1800
tattcgaaag gaacaattgc attggtggtt gtggggtgtg tagccttgtt gggtattata   1860
gccggaggaa tttcttacgc cagaaacaga ggaggtgagc gcgatgatga agacttggca   1920
ccaccacctc gttccacacg agaacggagg ctctcatcaa tgggcgaagg ttttgagaat   1980
gcctcatggg catcttctgt aagtatgatt cctagtgcac ctgctccgcc accttcgggc   2040
ggtatctggt cctaa                                                    2055
```

VIRUS-LIKE PARTICLES CO-EXPRESSING *TOXOPLASMA GONDII* IMC, ROP18, AND MIC8, AND PHARMACEUTICAL COMPOSITION COMPRISING THE SAME

RELATED APPLICATION

This application claims priority under 35 U.S.C. § 119 or 365 to Korean Application No. 10-2020-0001828, filed Jan. 7, 2020. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) Filename: 58301000000_CORRECTEDSEQUENCE-LISTING.txt; created Jun. 16, 2020, 21 KB in size.

STATEMENT REGARDING PRIOR DISCLOSURES BY THE INVENTOR OR A JOINT INVENTOR

The subject application claims the benefit of Korean Patent Application No. 10-2020-0001828 (filed on Jan. 7, 2020). The publication of Lee, Su-Hwa, et al., "Protective Immunity Induced by Incorporating Multiple Antigenic Proteins of *Toxoplasma gondii* Into Influenza Virus-Like Particles," Frontiers in Immunology, Vol. 9, Article 3073, Jan. 7, 2019 was published by an inventor or joint inventor of the subject application. The publication was published on Jan. 7, 2019, which is one year before the effective filing date of Jan. 7, 2020.

BACKGROUND

1. Field

The present invention relates to a virus-like particle (VLP) and uses thereof. Particularly, it relates to a virus-like particle for preventing or treating toxoplasmosis and a pharmaceutical composition comprising the same, wherein the virus-like particle comprises influenza virus matrix protein 1 as a structural protein and surface antigen proteins comprising an inner membrane complex, Rhoptry protein 18 and Microneme protein 8 derived from *Toxoplasma gondii.*

2. Description of the Related Art

*Toxoplasma gondii* is a apicomplexa belonging to a subclass of coccidia. *Toxoplasma gondii* is an obligare intercellular parasite and is a protozoan causing toxoplasmosis in humans and animals worldwide.

*Toxoplasma gondii* goes through five developmental stages which are oocyst, tachyzoit, bradyzoit, schizont and gametocyte. *Toxoplasma gondii* infection may occur when ingesting water or vegetables contaminated by the oocyst in feces of cats which are definitive hosts, or ingesting meats such as pork, lamb, beef, which are intermediate hosts in which *Toxoplasma gondii* is present as a cyst.

It is estimated that about more than a third of the world's population is infected with *Toxoplasma gondii*, and it is reported that the infection rate is 2 to 25% depending on the group in Korea.

Trophozoite of *Toxoplasma gondii* may infect the fetus across the placenta when the mother is infected with *Toxoplasma gondii*. By infection with *Toxoplasma gondii*, fetuses in early pregnancy may be miscarried or stillborn, and despite normal delivery congenital anomalies such as vision impairment, hydrocephalus, and mental weakness may occur in fetuses in mid- or late-pregnancy.

In addition, *Toxoplasma gondii* that infects healthy individuals may destroy immune system cells, reticular endothelial cells, etc. to cause diseases such as lymphadenitis, retinal choroiditis, and encephalomyelitis. Further, in immunodeficient host, the cysts proliferated in a brain may be activated to cause meningitis or retinal choroiditis.

Meanwhile, pyrimethamine, which is also used as a medicine for malaria, is most widely used as a medicine for toxoplasmosis, but its therapeutic effect is not good during pregnancy. In addition, spiramycin is used for a prophylaxis because its efficacy is not great.

Further, sulfamethoxazole, a sulfa drug used in combination with pyrimethamine, may cause bone marrow suppression which can reduce platelet count, and induce side effects such as allergic reactions, kidney disorders, blood disorders, nausea, and vomiting by combined administration of folic acid.

However, the therapeutic effect of sulfa drugs or pyrimethamine, which is the most widely used medicines against *Toxoplasma gondii*, is gradually decreasing due to increased resistance. Further, no vaccine has been developed to impart immunity against *Toxoplasma gondii* by producing antibodies.

Meanwhile, a virus-like particle which is morphologically similar to the actual virus structure has been proposed as a vaccine antigen against several viruses (Roldao A, Mellado M C, Castilho L R, Carrondo M J, Alves P M: Expert review of vaccines 2010, 9:1149-1176; Kang S M, Kim M C, Compans R W: Expert review of vaccines 2012, 11:995-1007; Kushnir N, Streatfield S J, Yusibov V: Vaccine 2012, 31:58-83).

A virus-like particle has been receiving a lot of attention recently as an antigen for use in immunogen compositions. A virus-like particle is morphologically similar to wild type viruses, and it contains one or more surface proteins to induce an immune response in a body. Since a virus-like particle lacks genetic materials, unlike wild-type viruses, it is non-infectious and very safe despite being able to activate an immune system.

The present inventors have tried to develop a novel virus-like particle which induces an immune response in a body and thus is safe, has no problem of resistance, and has excellent prevention and treatment effects for toxoplasmosis, unlike conventional therapeutic agents that directly act on *Toxoplasma gondii.*

SUMMARY

It is an object of the present invention to provide a new virus-like particle capable of inducing immune response against *Toxoplasma gondii* in a body, i.e., a virus-like particle for preventing or treating toxoplasmosis, comprising influenza virus matrix protein 1 as a structural protein and surface antigen proteins comprising an inner membrane complex, Rhoptry protein 18 and Microneme protein 8 derived from *Toxoplasma gondii*, and a use thereof.

In one aspect, the present invention provides a virus-like particle comprising influenza virus matrix protein 1 (M1); and surface antigen proteins comprising an inner membrane complex (IMC), Rhoptry protein 18 (ROP18) and Microneme protein 8 (MIC8) derived from *Toxoplasma gondii.*

In one embodiment, the influenza virus matrix protein 1 (M1) may consist of the amino acid sequence of SEQ ID NO: 1, the inner membrane complex (IMC) may consist of the amino acid sequence of SEQ ID NO: 2, the Rhoptry protein 18 (ROP18) may consist of the amino acid sequence of SEQ ID NO: 3, and the Microneme protein 8 (MIC8) may consist of the amino acid sequence of SEQ ID NO: 4.

In one embodiment, the influenza virus matrix protein 1 (M1) may be encoded by the nucleic acid sequence of SEQ ID NO: 5, the inner membrane complex (IMC) may encoded by the nucleic acid sequence of SEQ ID NO: 6, the Rhoptry protein 18 (ROP18) may encoded by the nucleic acid sequence of SEQ ID NO: 7, and the Microneme protein 8 (MIC8) may encoded by the nucleic acid sequence of SEQ ID NO: 8.

In another aspect, the present invention provides a pharmaceutical composition for preventing or treating toxoplasmosis comprising the virus-like particles as an active ingredient.

In one embodiment, the pharmaceutical composition is administered to the subject intranasally.

In one embodiment, the pharmaceutical composition is administered in combination with cytosine-phosphorothioate-guanine (CpG).

In one embodiment, the pharmaceutical composition is administered to a subject 1 to 3 times.

In another aspect, the present invention provides a method for preventing or treating toxoplasmosis, comprising administering the virus-like particles in an immunologically effective amount to a subject.

In another aspect, the present invention provides a composition comprising the virus-like particles for use in prevention or treatment of toxoplasmosis.

In another aspect, the present invention provides a use of the composition comprising the virus-like particles for manufacturing a medicine for preventing or treating toxoplasmosis.

In another aspect, the present invention provides an expression vector for preparing a virus-like particle comprising a nucleic acid sequence encoding influenza virus matrix protein 1 (M1); a nucleic acid sequence encoding an inner membrane complex (IMC); a nucleic acid sequence encoding Rhoptry protein 18 (ROP18); and a nucleic acid sequence encoding Microneme protein 8 (MIC8).

In another aspect, the present invention provides a host cell transformed with the expression vector.

In one embodiment, the host cell may be a microorganism, an animal cell, a plant cell, a cultured cell derived from an animal, or a cultured cell derived from a plant.

In another aspect, the present invention provides a method for preparing a virus-like particle, comprising transforming a host cell with the expression vector; and culturing the host cell to express the virus-like particle.

The virus-like particles of the present invention not only inhibit the production of inflammatory cytokines due to *Toxoplasma gondii* infection and inhibit the production of *Toxoplasma gondii* cysts in a mouse body, but also can provide a remarkably high level of immunity against *Toxoplasma gondii.*

The virus-like particles of the present invention simultaneously expressing three or more proteins derived from the *Toxoplasma gondii* can induce an excellent *Toxoplasma gondii*-specific antibody response, and promote the production of anti-inflammatory cytokines in an individual to reduce the inflammatory response. In addition, it can also effectively protect the individual by significantly reducing the size and number of *Toxoplasma gondii* cysts in the individual, thereby contributing to the survival and weight maintenance of the individual.

It should be understood that the effects of the present invention are not limited to the above-described effects, and include all effects that can be deduced from the configuration of the invention described in the detailed description or claims of the present invention.

BRIEF DESCRIPTION OF THE DRAWINGS

FIG. 6 shows the apoptosis levels in spleen of mice after challenge infection of a negative control (Naïve), a positive control (Naïve+Cha), TG1/TG4/TG6 VLP injection group (TG1/TG4/TG6+Cha), and TG146 VLP injection group (TG146+Cha).

FIGS. 7A-C shows the body weight changes and survival rates and the inhibition of parasite replication after challenge infection of a positive control (Naïve+Cha), TG1/TG4/TG6 VLP injection group (TG1/TG4/TG6+Cha), and TG146 VLP injection group (TG146+Cha): (a) Survival rate; (b) Body weight change; (c) Inhibition of parasite replication.

DETAILED DESCRIPTION

Figure 1A:
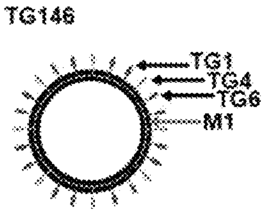
FIGS. 1A-1D show schematic diagrams and the results of western blot analysis of TG146 VLP that simultaneously expresses M1; and IMC, ROP18, and MIC8, and TG1/TG4/TG6 VLP in which a VLP comprising M1 and IMC (TG1) (TG1 VLP), a VLP comprising M1 and ROP8 (TG4) (TG4 VLP), and a VLP comprising M1 and MIC8 (TG6) (TG6 VLP) are combined in a ratio of 1:1:1: (A) Schematic diagram of TG146 VLP; (B) Schematic diagram of TG1/TG4/TG6 VLP; (C) Western blot results of TG146 VLP; (D) Western blot results of TG1/TG4/TG6 VLP.
Figure 1B:
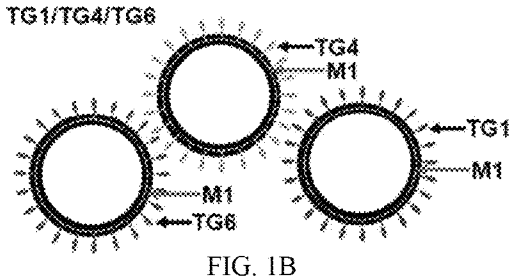

Hereinafter, the present invention will be described with reference to the accompanying drawings. However, the present invention can be implemented in several different embodiments, and is therefore not limited to the embodiments described herein.

When a part is said to "comprise" a certain component, this means that other components may be further provided rather than being excluded, unless otherwise specified.

Unless otherwise defined, molecular biology, microbiology, protein purification, protein engineering, and DNA sequencing and routine techniques commonly used in the field of recombinant DNA within the skill of the artisan can be performed. These techniques are known to those skilled in the art and are described in many textbooks and references.

Unless defined otherwise, all technical and scientific terms used herein have the same meaning as commonly understood by one of ordinary skill in the art.

Various scientific dictionaries including terms included herein are well known and available in the art. Although any methods and materials similar or equivalent to those described herein are found to be used in the practice or testing of the present invention, several methods and materials are described. Since various methods and materials can be used depending on the context used by those skilled in the art, the present invention is not limited to specific methodologies, protocols, and reagents.

As used herein, a singular form includes a plural form unless the context clearly dictates otherwise. Further, unless otherwise indicated, nucleic acids are written in 5' to 3' directions from left to right, and amino acid sequences are written in amino to carboxyl directions from left to right.

Hereinafter, the present invention will be described in more detail.

In one aspect, the present invention provides a virus-like particle comprising influenza virus matrix protein 1 (M1); and surface antigen proteins comprising an inner membrane complex (IMC), Rhoptry protein 18 (ROP18) and Microneme protein 8 (MIC 8) derived from *Toxoplasma gondii.*

The "virus-like particle (VLP)" of the present invention means a non-infectious viral subunit with or without viral proteins. For example, the virus-like particle may be completely devoid of DNA or RNA genome. In particular, virus-like particle according to an embodiment of the present invention may be prepared by genetic engineering methods, and may comprise matrix protein 1 (M1) derived from influenza virus as a core protein. Since the virus-like particle of the present invention can be produced by a genetic engineering method without a separate causative infectious agent, that is, *Toxoplasma gondii*, high productivity and economic feasibility can be realized.

The "influenza virus matrix protein 1 (M1)" of the present invention is a structural protein of influenza virus, and refers to a matrix protein that forms a coat inside the fat layer which is the envelope of the influenza virus. The influenza virus consists of subtypes named A, B, and C. The influenza virus is wrapped with a layer of matrix protein 1 (M1), which acts as a link between the core and the viral envelope, and the M1 protein can be widely used as a structural protein in the development of influenza virus-like particles.

The virus-like particle of the present invention may comprise influenza virus matrix protein 1 (M1) as a structural protein, and may comprise one or more surface antigen proteins derived from *Toxoplasma gondii* on the surface of the influenza virus matrix protein 1 (M1).

Since the virus-like particle of the present invention comprises surface antigen proteins derived from *Toxoplasma gondii* on its surface, it can induce an immune response specific to *Toxoplasma gondii* when it enters a specific individual. Thus, the virus-like particle of the present invention can impart immunity against *Toxoplasma gondii* to the individual.

The virus-like particle of the present invention can be prepared by methods well known in the art. For example, the virus-like particle of the present invention can be produced by transforming a predetermined host cell with a recombinant DNA molecule encoding a structural protein and surface antigen proteins, and then culturing the cells. The proteins expressed in the cells are assembled on the cell surface, and then can be discharged into a culture supernatant. The virus-like particle of the present invention acts as antigen in an individual and can present antigens to T or B immune cells through reaction with antigen presenting cells such as dendritic cells.

The virus-like particle of the present invention contains surface antigen proteins derived from *Toxoplasma gondii*, but since it does not contain a genetic material, it can't proliferate and is safe because it is non-toxic. Thus, the particle can be used as a vaccine against *Toxoplasma gondii*. The antigen proteins introduced on the surface of the virus-like particle of the present invention have a high antigenicity compared to a pure isolated recombinant protein and can induce an effective neutralizing antibody.

The "surface antigen protein" of the present invention is a basic element or minimum unit of recognition by each antibody or T cell receptor, and refers to a specific domain, region or molecular structure to which the antibody or T cell receptor binds. The surface antigen protein of the present invention may be derived from *Toxoplasma gondii*, and is not particularly limited as long as it can induce immune activity against *Toxoplasma gondii*.

In one embodiment, the surface antigen protein of the present invention may comprise various kinds of proteins such as SAG1 (Membrane-associated surface antigen), SAG2, GRA1 (secreted dense-granule protein), GRA2, GRA4, GRA7, MIC1 (Microneme protein), MIC2, MIC4, MIC6, MIC7, MIC8, MIC9, MIC10, MIC11, ROP1, ROP2, ROP3, ROP4, ROP5, ROP6, ROP7, ROP8, ROP9, ROP10, ROP11, ROP12, ROP13, ROP14, ROP15, ROP16, ROP17, ROP18, M2AP (MIC2 associated protein), AMA1 (*Plasmodium* apical membrane antigen 1), and BAG1 derived from *Toxoplasma gondii*, and preferably may comprise the inner membrane IMC, ROP18 and MIC8 at the same time.

The "inner membrane complex" of the present invention is a peripheral membrane system consisting of flattened alveolar sacs underlying the plasma membrane, and is connected to the cytoskeletal network.

The "inner membrane complex" of the present invention plays an important role in parasitic replication, cell motility, and host cell invasion. The inner membrane complex is involved in the formation of new cells in *Toxoplasma gondii*, and replicated chromatin and organelles are closely related to the assembly of the skeleton as a cell division process (Sheffield and Melton, 1968).

The "Rhoptry protein 18" of the present invention is a type of Rhoptry protein derived from *Toxoplasma gondii* that is involved in the invasion of active parasites into host cells, and is a protein essential for *Toxoplasma gondii* to be parasitic on host cells. Further, the protein is closely related to cell recognition, invasion, and virulence based on genetic destruction. Various Rhoptry proteins are known, and may be potential antigen targets that induce an effective immune response of the host cell against *Toxoplasma gondii.*

The "Microneme protein 8" of the present invention is a protein that is essential for *Toxoplasma gondii* to be parasitic on host cells, and is closely related to cell recognition, invasion, and virulence based on genetic destruction. Various types of Microneme proteins are known, and have been studied as potential antigen targets that induce an effective immune response of the host cell against *Toxoplasma gondii.*

In particular, the present inventors confirmed that a virus-like particle vaccine that simultaneously expresses the inner membrane complex (IMC), Rhoptry protein 18 (ROP18), and Microneme protein 8 (MIC8) inhibits the production of inflammatory cytokines due to infection and the production of parasites in a mouse body. In addition, it was confirmed that the vaccine can provide a high level of immunity against *Toxoplasma gondii* when introduced into an individual as a form fused with influenza virus matrix protein 1 (M1).

In particular, compared to a virus-like particle vaccine that expresses the inner membrane complex (IMC), Rhoptry protein 18 (ROP18), or Microneme protein 8 (MIC8) alone, the virus-like particle vaccine that simultaneously expresses the inner membrane complex (IMC), Rhoptry protein 18 (ROP18), and Microneme protein 8 (MIC8) can further increase the level of *Toxoplasma gondii*-specific antibody response and the level of T cell and B cell responses in the subject after immunization, and the survival rate of the subject. Further, it can further reduce the subject's weight loss rate and parasite burden.

In one embodiment, influenza virus matrix protein 1 (M1) of the present invention may consist of the amino acid sequence of SEQ ID NO: 1, the inner membrane complex (IMC) may consist of the amino acid sequence of SEQ ID NO: 2, and the Rhoptry protein 18 (ROP18) may consist of the amino acid sequence of SEQ ID NO: 3, and the Microneme protein 8 (MIC 8) may consist of the amino acid sequence of SEQ ID NO: 4.

SEQ ID NOs: 1 to 4 of the present invention are known sequences and are represented as follows.

Amino acid sequence of influenza virus matrix protein 1 (M1) (GenBank Accession No. AB021712.1)

<SEQ ID NO: 1>

MSLLTEVETYVLSIIPSGPLKAEIAQRLEDVFAGKNTDLEVLMEWLKTR

PILSPLTKGILGFVFTLTVPSERGLQRRRFVQNALNGNGDPNNMDKAVK

LYRKLKREITFHGAKEISLSYSAGALASCMGLIYNRMGAVTTEVAFGLV

CATCEQIADSQHRSHRQMVTTTNPLIRHENRMVLASTTAKAMEQMAGSS

EQAAEAMEVASQARQMVQAMRTGTHPSSSAGLKNDLLENLQAYQKRMGV

QMQRFK

Amino acid sequence of inner membrane complex (IMC) (GenBank Accession No. ADV15617)

<SEQ ID NO: 2>

MGNTACCGFDSDSTADLEIGREGEVRSRKPIQVSKEAFDNWMNRYEAGD

TMEVLEPDGHRIECNLKIDRPKNFMNLTFNQKVRPIQLDDIAAVLYGSD

-continued

PRSSECADSKMLRNPCVVGFRLASSGRAIAFSFKDITDAQCFVSFLDDE

IKKNQESNKSSASNDRN

Amino acid sequence of Rhoptry protein 18 (ROP18) (GenBank Accession No. CAJ27113)

<SEQ ID NO: 3>

MFSVQRPPLTRTVVRMGLATLLPKTACLAGLNVALVFLLFQVQDGTGIT

LGPSKLDSKPTSLDSQQHVADKRWLATVGHYKHLAGATESTRDVSLLEE

RAQHRVNAQETNQRRTIFQRLLNLLRRRERDGEVSGSAADSSSRPRLSV

RQRLAQLWRRAKSLFKRGIRRYFPQGRNRQRSLRAQRRRSELVFEKADS

GCVIGKRILAHMQEQIGQPQALENSERLDRILTVAAWPPDVPKRFVSVT

TGETRTLVRGAPLGSGGFATVYEATDVETNEELAVKVFMSEKEPTDETM

LDLQRESSCYRNFSLAKTAKDAQESCRFMVPSDVVMLEGQPASTEVVIG

LTTRWVPNYFLLMMRAEADMSKVISWVFGDASVNKSEFGLVVRMYLSSQ

AIKLVANVQAQGIVHTDIKPANFLLLKDGRLFLGDFGTYRINNSVGRAI

GTPGYEPPERPFQATGITYTFPTDAWQLGITLYCIWCKERPTPADGIWD

YLHFADCPSTPELVQDLIRSLLNRDPQKRMLPLQALETAAFKEMDSVVK

GAAQNFEQQEHLHTE

Amino acid sequence of Microneme protein 8 (MIC 8) (GenBank Accession No. AAK19757)

<SEQ ID NO: 4>

MKANRIWCFFAWRMVVRASFLKEMDSIFVSAIRQNVQHTHSALLAKLKE

PPDPDDENSWLCRISKKYDACGSREYSDKGLKGTYCPEDFCCSKTACFY

-continued

GSCGSWCHDNWALCSSSIIYHDEYSYGKCNCKRFQENCDVNAICVHANR

EDGGAYCQCKEGYWGDGKSCKIDFCQLQPCGAGTCTRTDEGYKCDCPET

HKLIVVEDKETCKAKPDFCAEEPCGPPSMVENCVNTDDSYECVCKQGYE

VRNGRCEEIDLCADKPCGPDEGVHECVTERQPKLRYRCTCKAGFDLTTL

PDGVSQKCLKNFCYEEPCGTRDLVESCKSKAYGYSCLCAAGAMVQVING

KEKCIKADLCRNDPCGPETAVIQCYSHGTSYRCLCKAGYTEVFVNGKSS

CQKGDPCTLNMCGGNEAVQECTTDGTAYGCTCKPGYSIAIKHGQKFCNP

EEECASHCGSAAAVKSCEILDSGGYQCTCNPGYVMRYSDYVKGCVEGNQ

CSLNPCGEQEAVQRCIPEGDTYDCECNPGFVKRVLPDGNFICADPASCV

GNPCGSSDAVDACIAGTSTYTCRCKDGYTPQSIGSKLQCLPESTDQTDF

DSKHKPEDNKGRYSKGTIALVVVGCVALLGIIAGGISYARNRGGERIDD

EDLAPPPRSTRERRLSSMGEGFENASWASSVSMIPSAPAPPPSGGIWS

Further, the influenza virus matrix protein 1 (M1) of the present invention may be encoded by the nucleic acid sequence of SEQ ID NO: 5, the inner membrane complex (IMC) may be encoded by the nucleic acid sequence of SEQ ID NO: 6, the Roptry protein 18 (ROP18) may be encoded by the nucleic acid sequence of SEQ ID NO: 7, and the Microneme protein 8 (MIC8) may be encoded by the nucleic acid sequence of SEQ ID NO: 8.

SEQ ID NOs: 5 to 8 of the present invention are known sequences and are represented as follows.

<SEQ ID NO: 5> Nucleic acid sequence of influenza virus matrix protein 1 (M1) (GenBank Accession No. EF467824)

```
   1  agcgaaagca ggtagatatt gaaagatgag tcttctaacc gaggtcgaaa cgtacgtact

  61  ctctatcatc ccgtcaggcc ccctcaaagc cgagatcgca cagagacttg aagatgtctt

 121  tgcagggaag aacaccgatc ttgaggttct catggaatgg ctaaagacaa gaccaatcct

 181  gtcacctctg actaagggga ttttaggatt tgtgttcacg ctcaccgtgc ccagtgagcg

 241  aggactgcag cgtagacgct ttgtccaaaa tgcccttaat gggaacgggg atccaaataa

 301  catggacaaa gcagttaaac tgtataggaa gctcaagagg gagataacat tccatggggc

 361  caaagaaatc tcactcagtt attctgctgg tgcacttgcc agttgtatgg gcctcatata

 421  caacaggatg gggctgtga ccactgaagt ggcatttggc ctggtatgtg caacctgtga

 481  acagattgct gactcccagc atcggtctca taggcaaatg gtgacaacaa ccaatccact

 541  aatcagacat gagaacagaa tggttttagc cagcactaca gctaaggcta tggagcaaat

 601  ggctggatcg agtgagcaag cagcagaggc catggaggtt gctagtcagg ctagacaaat

 661  ggtgcaagcg atgagaacca ttggaactca tcctagctcc agtgctggtc tgaaaaatga

 721  tcttcttgaa aatttgcagg cctatcagaa acgaatgggg gtgcagatgc aacggttcaa

 781  gtgatcctct cactattgcc gcaaatatca ttgggatctt gcacttgaca ttgtggattc

 841  ttgatcgtCt tttttcaaa tgcatttacc gtcgctttaa atacggactg aaaggagggc

 901  cttctacgga aggagtgcca aagtctatga gggaagaata tcgaaaggaa cagcagagtg

 961  ctgtggatgc tgacgatggt cattttgtca gcatagagct ggagtaaaaa actaccttgt

1021  ttctact
```

-continued

<SEQ ID NO: 6> Nucleic acid sequence of inner membrane complex (IMC) (GenBank Accession No. HQ012579)

```
  1   atggggaaca cggcgtgctg cggtttcgac agtgactcta ctgctgacct cgagatcggt
 61   cgagaggggg aagtgcggag tcgcaaacca attcaggtat ccaaagaggc gtttgacaac
121   tggatgaatc gttatgaggc cggagacacg atggaagtgc tttttcctga tggtcaccga
181   attgagtgta acttgaaaat cgaccgaccg aaaaacttca tgaatctcac cttcaatcag
241   aaagtaagac ccatccagct ggatgacatt gcagctgtcc tatatggctc ggatcctcgc
301   agttccgaat gcgcagatag caaaatgctg cgaaacccct gtgtcgtggg cttccgcctc
361   gcgagctctg gacgagccat cgcgttttct tttaaagaca tcacggacgc gcagtgtttt
421   gtgtctttcc tggacgacga aatcaagaag aatcaggagt caaacaagtc ttcagcaagc
481   aacgacagaa actaa
```

<SEQ ID NO: 7> Nucleic acid sequence of Rhoptry protein 18 (ROP18) (GenBank Accession No. AM075204)

```
   1   atgttttcgg tacagcggcc acctcttacg cgtaccgtcg tccgaatggg tttagcgact
  61   cttctcccga agacagcctg tcttgcgggg ttaaatgtag cgcttgtctt cctgctcttc
 121   caagtccagg atgggaccgg aatcacactt ggtccttcaa aactcgactc caaaccgaca
 181   agtttggatt cgcaacagca cgttgctgac aagcggtggc ttgctacagt tggccactac
 241   aaacatttag caggagcgac agaaagcact cgagacgttt cattgctgga ggaaagggct
 301   caacaccggg taaatgcgca agaaacaaac caacggcgca cgatttttca gaggcttctg
 361   aatctcttga gacggagaga aagagatggt gaagtctcgg gttccgcagc tgatagctcc
 421   tcgagacccc gtctgtccgt acgacagagg cttgctcaac tttggcgtag agcgaaatcg
 481   ttattcaaac gcggaatccg gaggtacttt cctcaagggc gtaaccgaca gcgaagtttg
 541   cgggcacaaa gacggcgatc tgaattggtt tttgagaagg cggattctgg atgcgtcatc
 601   ggcaaacgca tcctggcgca catgcaagaa caaatcgggc agcctcaagc gctagaaaat
 661   agtgaacgac tggatagaat tctgactgtc gccgcctggc ctccggacgt tccaaaaaga
 721   tttgtttctg tgactaccgg tgaaacccgg acgctggtga gaggtgcacc ccttggctct
 781   ggtggattcg ccactgtata tgaggctaca gacgtggaga cgaatgaaga gttggctgtt
 841   aaggttttca tgtcagaaaa ggagcccacc gatgagacta tgcttgactt gcagagggag
 901   tcgtcctgct acaggaactt tagtctagcc aagacggcga aggatgccca ggaaagctgt
 961   agattcatgg ttcctagtga tgttgtgatg ttagagggac agccagcatc cacagaggtc
1021   gtgattggtt tgacgactcg gtgggtacca aactattttc ttctcatgat gcgggcagaa
1081   gcggacatga gcaaagtcat ttcatgggta tttggagatg cgtctgtcaa taaaagtgaa
1141   tttggcctgg tcgttcgaat gtacctatcc agtcaggcaa tcaaactagt ggccaatgtt
1201   caagctcagg gaattgtgca tacggatatc aaaccggcga atttcctcct cttgaaagac
1261   ggtcgcctgt ttctcggcga cttcggaacg tatagaatca ataattcggt tggacgcgcg
1321   ataggtactc ccggttacga gcctccggag cgaccgtttc aggctacagg catcacctat
1381   acattcccca ctgacgcgtg gcaactcggt ataactttgt actgcatctg gtgcaaggaa
1441   cgtccaactc cggccgacgg catctgggac tacttacact tcgcagattg tccttccacg
1501   cctgagctgg ttcaagacct catccgaagc ctcttgaatc gagatcctca gaaacggatg
1561   ctcccgctac aagccttgga gacagcagcg tttaaagaga tggattcagt agtaaaaggc
1621   gccgcgcaaa acttcgaaca gcaggaacat ctccacacag aataa
```

-continued

<SEQ ID NO: 8> Nucleic acid sequence of Microneme protein 8 (MIC 8)
(GenBank Accession No. AF353165)

```
   1 atgaaggcca atcgaatatg gtgttttttt gcgtggcgta tggttgtgcg ggcctcattt
  61 ctgaaagaga tggacagcat tttcgtttct gctatccgac agaatgtaca gcatactcat
 121 tctgcccttc tcgccaaact gaaggaaccc ccagatccag atgatgagaa ctcttggctt
 181 tgtcgaatat caaaaaaata tgacgcatgc ggtagcaggg aatattccga taagggcctc
 241 aaagggacgt actgtcccga ggatttttgc tgtagcaaga cggcatgttt ttacggttca
 301 tgtgggagtt ggtaccacga caactgggct ctgtgcagct catctataat ctaccacgac
 361 gagtacagtt acgggaaatg caactgtaaa cggtttcaag aaaactgtga tgtgaatgca
 421 atttgtgtgc atgcgaacag agaggatggc ggtgcgtatt gtcagtgcaa ggaaggatat
 481 tggggtgatg gtaaatcgtg caagattgac ttctgccaac tgcagccctg tggtgcaggg
 541 acctgcacca ggacggatga aggatacaag tgtgattgcc cagaaactca caagcttatt
 601 gtcgttgaag acaaagagac gtgcaaggca aaaccggact tttgcgcgga agagccttgc
 661 ggaccaccct ctatggttga aaattgcgtg aacaccgatg acagctacga atgtgtttgc
 721 aaacaggggt atgaagtgag gaacggtcgg tgcgaagaaa ttgacttatg cgcggacaag
 781 ccatgtgggc cagatgaggg tgtgcatgag tgtgtaacag agaggcaacc gaaattaagg
 841 tacagatgca cgtgcaaggc aggattcgat ttgaccacct tgcctgatgg tgtttcccag
 901 aagtgcctga agaacttctg ttacgaggag ccctgcggca cccgggacct agttgaaagc
 961 tgtaagtcaa aggcatatgg atactcgtgt ttgtgtgcgg caggtgccat ggttcaagtg
1021 attaacggaa aagaaaagtg catcaaggcg gacttgtgcc gcaatgatcc gtgtggtcca
1081 gagacagcag tgattcaatg ttactctcat ggcaccagct ataggtgttt gtgcaaagca
1141 ggctacactg aagtttttgt taacgggaag agttcatgtc aaaagggcga cccatgcact
1201 ctgaacatgt gtggcggtaa cgaagcggtc caggagtgca caactgatgg cacggcgtac
1261 gggtgtacct gcaagccagg ctattcgata gccattaagc atggtcagaa gttttgcaac
1321 cctgaagagg agtgtgcttc tcattgtggc tcggcagctg cagtgaaaag ctgtgaaata
1381 cttgactctg gcggatacca gtgtacatgc aatccaggat acgtcatgag atacagcgac
1441 tatgtaaaag gatgcgtcga gggaaatcag tgttctctca atccttgtgg ggagcaggaa
1501 gccgtgcaaa ggtgcattcc tgaaggtgac acgtatgatt gcgagtgcaa tccggggttc
1561 gtcaaaagag tcttgccgga tgggaatttc atttgcgccg atccagcgag ctgtgtaggg
1621 aatccctgtg gtagctcaga tgcggtcgat gcgtgcattg ccgggactag cacgtataca
1681 tgcaggtgta aggacggata cacacctcag tcaattgggt caaagttgca gtgtttacca
1741 gaaagcactg atcagacaga tttcgattcc aaacacaaac cagaggacaa caaaggtcga
1801 tattcgaaag gaacaattgc attggtggtt gtggggtgtg tagccttgtt gggtattata
1861 gccggaggaa tttcttacac cagaaacaga ggaggtgagc gcgatgatga agacttggca
1921 ccaccacctc gttccacacg agaacggagg ctctcatcaa tgggcgaagg ttttgagaat
1981 gcctcatggg catcttctgt aagtatgatt cctagtgcac ctgctccgcc accttcgggc
2041 ggtatctggt cctaa
```

Influenza virus matrix protein 1 (M1); inner membrane complex (IMC), Rhoptry protein 18 (ROP18), or Microneme protein 8 (MIC8) of the present invention includes a functional equivalent of a protein consisting of the amino acid sequences of SEQ ID NOs: 1-4, respectively.

The "functional equivalent" means a protein which has substantially the same physiological activity and a sequence homology of at least 70%, preferably 80% or more, more preferably 90% or more, and more preferably 95% or more to any one of the amino acid sequences of SEQ ID NOs: 1-4 as a result of the addition, substitution or deletion of amino acids.

The "substantially the same physiological activity" means an activity as a virus-like particle capable of inducing a specific immune response against *Toxoplasma gondii* due to its structural and functional homology with the influenza virus matrix protein 1 (M1); the inner membrane complex (IMC), Rhoptry protein 18 (ROP18), or Microneme protein 8 (MIC8).

In another aspect, the present invention provides a pharmaceutical composition for preventing or treating toxoplasmosis comprising the virus-like particles of the present invention as an active ingredient.

The Toxoplasmosis includes all diseases and symptoms that can be caused by infection with *Toxoplasma gondii. Toxoplasma gondii* can be parasitic in various parts of the body, for example, lymph glands, brain, lungs, myocardium, spleen, bone marrow, kidneys, adrenal glands, nervous system, etc. Further, tachyzoite can divide and proliferate actively in reticuloendotheliar cells and endothelial cells of circulatory system to cause tissue necrosis. In addition, it may cause various diseases and symptoms depending on the site of infection, which include for example, lymphadenitis, retinochoroiditis, meningitis, encephalomyelitis, hepatitis, myositis, myocarditis, pneumonia, renal tubular disease, etc., but are not limited thereto.

The pharmaceutical composition of the present invention comprises the virus-like particles of the present invention as active ingredients. For example, the pharmaceutical composition of the present invention may be used in various purified forms of virus-like particles, such as a transformed host cell itself or a dry powder form of transformed cells, a culture solution of transformed cells, or a concentrate thereof.

The pharmaceutical composition may comprise one or more supplementary ingredient selected from the group consisting of aluminum hydroxide, aluminum phosphate, liposomes, iscom adjuvant, synthetic glycopeptide, carboxypolymethylene, bacterial cell wall, bacterial cell wall derivatives, bacterial vaccine, animal poxvirus protein, subviral particle adjuvant, cholera toxin, N, N-dioctadecyl-N',N'-bis (2-hydroxyethyl)-propanediamine, monophosphoryl lipid A, dimethyldioctadecyl-ammonium bromide and mixtures thereof.

Further, the pharmaceutical composition of the present invention may comprise a medically acceptable carrier. The “medically acceptable carrier” may include any and all solvents, dispersion media, coatings, adjuvants, stabilizers, diluents, preservatives, antibacterial agents, antifungal agents, isotonic agents, adsorption retardants, etc., but is not limited thereto.

Carriers, excipients, and diluents that may be used in the pharmaceutical composition may include lactose, dextrose, sucrose, sorbitol, mannitol, xylitol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, etc., but are not limited thereto.

In addition, the pharmaceutical composition of the present invention can be prepared by a method commonly used in the art to which the present invention pertains. The pharmaceutical composition of the present invention may be prepared into oral or parenteral preparations, preferably into an injection solution, which is a parenteral preparation, and may be administered by intradermal, intramuscular, intraperitoneal, intravenous, subcutaneous, intranasal or epidural route. Preferably, the pharmaceutical composition of the present invention is administered to a subject intramuscularly or intranasally. More preferably, the pharmaceutical composition of the present invention is administered intranasally to a subject.

In particular, when the pharmaceutical composition of the present invention is administered intranasally, the levels of T cell and B cell responses in the spleen and mesenteric lymph node (MLN) of a subject after administration may be further increased, and the level of inflammatory cytokines, the size and count of cysts in a brain and the weight loss rate of a subject may be further reduced.

Specifically, the pharmaceutical composition of the present invention can be formulated into oral dosage forms such as powders, granules, tablets, capsules, suspensions, emulsions, syrups, aerosols, etc. and sterile injectable solutions according to each conventional method and used.

Commonly used diluents or excipients such as fillers, extenders, binders, wetting agents, disintegrating agents, and surfactants may be used for formulation.

Solid preparations for oral administration include tablets, pills, powders, granules, capsules, etc. These solid preparations may be used with at least one excipient, such as starch, calcium carbonate, sucrose, lactose, gelatin, and the like. In addition, lubricants such as magnesium stearate and talc may be used in addition to the excipients. As a liquid preparation for oral administration, a suspension, a liquid for internal use, an emulsion, or a syrup may be used, and various excipients such as wetting agents, sweeteners, fragrances, and preservatives may be used in addition to commonly used diluents such as water and liquid paraffin.

As a preparation for parenteral administration, sterilized aqueous solutions, non-aqueous agents, suspensions, emulsions, and lyophilized preparations may be used. For non-aqueous preparations, and suspensions, propylene glycol, polyethylene glycol, vegetable oils such as olive oil, injectable esters such as ethyl oleate, and the like may be used.

The pharmaceutical composition of the present invention may be administered to a subject in an immunologically effective amount. The “immunologically effective amount” refers to an amount sufficient to exhibit a prophylactic or therapeutic effect for toxoplasmosis and an amount that does not cause side effects or serious or excessive immune responses. The precise dosage depends on the specific immunogen to be administered, and can be easily determined by those skilled in the art depending on factors well known in the art, such as age, weight, health, gender, and sensitivity to drugs of the subject, administration route, administration method, etc. For example, it can be administered at 0.0001 to 50 mg/kg or 0.001 to 50 mg/kg per day. It may be administered once or several times a day. The above dosage does not limit the scope of the present invention in any way.

When administered as a vaccine composition to a subject, the pharmaceutical composition of the present invention may be administered 1 to 3 times, preferably 2 to 3 times, more preferably 3 times. As the number of administrations of the pharmaceutical composition of the present invention increases, the level of antibody response can be further increased, and the level of inflammatory cytokines and the count of cysts in a brain can be further reduced.

In addition, the pharmaceutical composition of the present invention may comprise additional adjuvants capable of enhancing the immune activity of the virus-like particles, or may be administered to a subject in combination with additional adjuvants simultaneously or sequentially. Adjuvants that can be used with the virus-like particles of the present invention may be conventional adjuvants used in the art to improve the immunity of vaccine compositions, such as cytosine-phosphorothioate-guanine (CpG), flagellin, aluminum hydroxide, monophosphoryl lipid A, glucopyranosyl lipid A, cholera toxin, QS21 (*Quillaja saponaria*), etc. Preferably, the adjuvant comprises cytosine-phosphorothioate-guanine (CpG).

Specifically, when the pharmaceutical composition of the present invention is administered in combination with cytosine-phosphorothioate-guanine (CpG), the level of *Toxoplasma gondii*-specific antibody response in a subject and the levels of T cell and B cell responses after administration can be significantly elevated, and the level of inflammatory cytokines, the size and count of cysts in a brain, and the body weight loss rate of a subject can be significantly reduced.

In another aspect, the present invention provides a use of the virus-like particles for preventing or treating toxoplasmosis and a use of the virus-like particles for manufacturing therapeutic agents for the disease.

Specifically, the present invention relates to a composition comprising the virus-like particles for use in the prevention or treatment of toxoplasmosis.

The present invention also relates to the use of a composition comprising the virus-like particles for the manufacture of a medicament for the prevention or treatment of toxoplasmosis.

In another aspect, the present invention provides a method for preventing or treating toxoplasmosis comprising administering the virus-like particles in an immunologically effective amount to a subject.

Specifically, the present invention relates to a method for preventing or treating toxoplasmosis comprising administering the virus-like particles in an immunologically effective amount to a subject in need of prevention or treatment of toxoplasmosis.

In another aspect, the present invention provides an expression vector for preparing the virus-like particles, comprising a nucleic acid sequence encoding influenza virus matrix protein 1 (M1); a nucleic acid sequence encoding inner membrane complex (IMC); a nucleic acid sequence encoding Rhoptry protein 18 (ROP18); and a nucleic acid sequence encoding Microneme protein 8 (MIC8).

The expression vector of the present invention refers to a nucleic acid molecule used to transport a nucleic acid fragment linked thereto. The expression vector of the present invention may include, but is not limited to, bacteria, plasmids, phages, cosmids, episomes, viruses, and insertable DNA fragments (i.e., fragments that can be inserted into a host cell genome by homologous recombination). The plasmid is a kind of vector and refers to a circular double-stranded DNA loop wherein additional DNA fragment can be linked. In addition, viral vectors can link additional DNA into a viral genome.

The expression vector of the present invention means a vector capable of directing the expression of a gene encoding a desired protein operably linked. In general, since the expression vector is in the form of a plasmid in use of recombinant DNA technology, the terms plasmid and vector can be used interchangeably. However, it may also include other types of expression vectors that perform the same function, such as viral vectors.

For example, the expression vector may be pET-3a-d, pET-9a-d, pET-11a-d, pET-12a-c, pET-14b, pET-15b, pET-16b, pET-17b, pET-17xb, pET-19b, pET-20b(+), pET-21a-d (+), pET-22b(+), pET-23a-d(+), pET-24a-d(+), pET-25b(+), pET-26b(+), pET-27b(+), pET-28a-c(+), pET-29a-c(+), pET-30a-c(+), pET-30 Ek/LIC, pET-30 Xa/LIC, pET-31b(+), pET-32a-c(+), pET-32 Ek/LIC, pET-32 Xa/LIC, pET-33b (+), pET-34b(+), pET-35b(+), pET-36b(+), pET-37b(+), pET-38b(+), pET-39b(+), pET-40b(+), pET-41a-c(+), pET-41 Ek/LIC, pET-42a-c(+), pET-43.1a-c(+), pET-43.1 Ek/LIC, pET-44a-c(+), pRSETA, pRSETB, pRSETC, pESC-HIS, pESC-LEU, pESC-TRP, pESC-URA, Gateway pYES-DEST52, pAO815, pGAPZ A, pGAPZ B, pGAPZ C, pGAPa A, pGAPa B, pGAPa C, pPIC3.5K, pPIC6 A, pPIC6 B, pPIC6 C, pPIC6a A, pPIC6a B, pPIC6a C, pPIC9K, pYC2/CT, pYD1 Yeast Display Vector, pYES2, pYES2/CT, pYES2/NT A, pYES2/NT B, pYES2/NT C, pYES2/CT, pYES2.1, pYES-DEST52, pTEF1/Zeo, pFLD1, PichiaPink™, p427-TEF, p417-CYC, pGAL-MF, p427-TEF, p417-CYC, PTEF-MF, pBY011, pSGP47, pSGP46, pSGP36, pSGP40, ZM552, pAG303GAL-ccdB, pAG414GALccdB, pAS404, pBridge, pGAD-GH, pGAD T7, pGBK T7, pHIS-2, pOBD2, pRS408, pRS410, pRS418, pRS420, pRS428, yeast micron A form, pRS403, pRS404, pRS405, pRS406, pYJ403, pYJ404, pYJ405 or pYJ406, but is not limited thereto.

Meanwhile, the expression vector of the present invention is introduced into a host cell, and the host cell transformed with the introduced vector can produce the virus-like particles. At this time, the vector may comprise a promoter recognized by the host organism.

The promoter may be selected from the group consisting of SBE4, 3TP, PAI-1, p15, p21, CAGA12, hINS, A3, NFAT, NFKB, AP1, IFNG, IL4, IL17A, IL10, GPD, TEF, ADH, CYC, INU1, PGK1, PHO5, TRP1, GAL1, GAL10, GUT2, tac, T7, T5, nmt, fbp1, AOX1, AOX2, MOX1 and FMD1 promoter, but may be varied depending on various variables such as host cells or expression conditions.

The nucleic acid sequence encoding the virus-like particle of the present invention can be operably linked to the promoter sequence. The term "operably linked" means that one nucleic acid fragment is linked with another nucleic acid fragment so that its function or expression is affected by another nucleic acid fragment. That is, the gene encoding the virus-like particle of the present invention can be operably linked to a promoter in the vector to regulate its expression.

Meanwhile, the expression vector of the present invention may further comprise additional regulatory sequences. The regulatory sequence may be, but is not limited to, the Shine-Dalgarno sequence of the replicase gene of the phage MS-2 and the Shine-Dalgarno sequence of cII of the bacteriophage lambda.

In addition, the expression vector of the present invention may comprise an appropriate marker gene required to select transformed host cells. The marker gene may be an antibiotic resistance gene or a fluorescent protein gene, and the antibiotic resistance gene may be selected from the group consisting of a hygromycin resistance gene, a kanamycin resistance gene, a chloramphenicol resistance gene, and a tetracycline resistance gene, but is not limited thereto. The fluorescent protein gene may be selected from the group consisting of a yeast-enhanced green fluorescent protein (yEGFP) gene, a green fluorescent protein (GFP) gene, a blue fluorescent protein (BFP) gene, and a red fluorescence protein (RFP) gene, but is not limited thereto.

In another aspect, the present invention provides a host cell transformed with the expression vector of the present invention. The host cell of the present invention means any organism that can be infected by a virus and immunized by virus-like particles. The host cell of the present invention may be metabolically engineered.

In one embodiment, the host cell of the present invention may be a microorganism, an animal cell, a plant cell, a cultured cell derived from an animal, or a cultured cell derived from a plant. The suitable host cell may be a naturally occurring or wild-type host cell, or may be a modified host cell. The wild-type host cell may be a host cell that has not been genetically modified by a recombination method.

The type of the host cell of the present invention is not particularly limited if it can be transformed by an engineering method to efficiently express a specific gene, and it may be preferably an insect cell. The insect cell may be any cell developed or commercially available as a host system for gene expression and it may be one or more selected from the group consisting of *Spodoptera frugiperda* SF21, SF9, *Trichoplusia ni, Anticarsa gemmitalis, Bombyx mori, Estigmene acrea, Heliothis virescens, Leucania separata, Lymantria dispar, Malacasoma disstria, Mammestra brassicae, Manduca sexta, Plutella zylostella, Spodoptera exigua* and *Spodoptera littorlis*, but is not limited thereto.

The "metabolically engineered" or "metabolic engineering" may involve a reasonable pathway design and assembly of biosynthetic genes, operon-related genes, and control elements for these nucleic acid sequences for the production of a desired metabolite such as alcohol or protein in a microorganism.

The "metabolically engineered" may further comprise optimization of metabolic flux through the regulation and optimization of transcription, translation, protein stability and protein functionality using genetic engineering and appropriate culture conditions.

The biosynthetic gene may be foreign to the host, or may be heterologous to the host (for example, microorganism) by being modified by mutagenesis, recombination or association with a heterologous expression control sequence in endogenous host cells. Suitable culture conditions may include conditions such as culture medium pH, ionic strength, and nutrient content, temperature, contents of oxygen, carbon dioxide, and nitrogen, humidity, and other culture conditions that enable the production of compounds by metabolism of the microorganisms. Culture conditions suitable for microorganisms capable of functioning as host cells are well known in the art.

Thus, the "metabolically engineered" or "modified" host cell can be produced by introducing genetic materials into a selected host or parent microorganism to modify or alter cell physiology and biochemistry. Through the introduction of genetic materials, parent microorganisms can acquire new properties, such as the ability to produce new intracellular metabolites or higher amounts of intracellular metabolites.

For example, the introduction of genetic materials into parent microorganisms can result in new or modified ability to produce chemical substances. The genetic materials introduced into the parent microorganism comprise a gene or part of a gene encoding one or more enzymes involved in the biosynthetic pathway for the production of chemical substances, and may comprise additional components for the expression of these genes or expression control, such as a promoter sequence.

The "altered host cell" refers to a genetically designed host cell, in which a desired protein can be produced at a level of expression or at a level greater than the level of expression or expressed at a level of expression greater than the level of expression of the desired protein in the unaltered or wild-type host cell grown under essentially the same growth conditions. The "modified host cell" means a wild type or an altered host cell genetically designed to overexpress a gene encoding a desired protein. The modified host cell can express the desired protein at a higher level than the wild-type or altered parent host cell.

Meanwhile, the "transformation" refers to a method of transporting the vector into a microorganism or a specific cell, and when a cell to be transformed is a prokaryotic cell, the transformation may be performed by $CaCl_2$ method (Cohen, S. N. et al., Proc. Natl. Acad. Sci. USA, 9: 2110-2114 (1973)), Hanahan method (Cohen, S. N. et al., Proc. Natl. Acad. Sci. USA, 9: 2110-2114 (1973); and Hanahan, D., J. Mol. Biol., 166: 557-580 (1983)) and electroporation (Dower, W. J. et al., Nucleic. Acids Res., 16: 6127-6145 (1988)).

When a cell to be transformed is a eukaryotic cell, the transformation may be performed by microinjection (Capecchi, M. R., Cell, 22: 479 (1980)), calcium phosphate precipitation (Graham, F. L. et al., Virology, 52: 456 (1973)), electroporation (Neumann, E. et al., EMBO J., 1: 841 (1982)), liposome-mediated transfection (Wong, T. K. et al., Gene, 10:87 (1980)), DEAE-Dextran transfection (Gopal, Mol. Cell. Biol., 5: 1188-1190 (1985)), and gene bombardment (Yang et al., Proc. Natl. Acad. Sci., 87: 9568-9572 (1990)), but is not limited thereto.

For transformation of fungi such as yeast, the transformation may be performed by methods using lithium acetate (RD Gietz, Yeast 11, 355360 (1995)) and heat shock (Keisuke Matsuura, Journal of Bioscience and Bioengineering, Vol. 100, 5; 538-544 (2005)) and electroporation (Nina Skolucka Asian, Pacific Journal of Tropical Biomedicine, 94-98 (2011)), but is not limited thereto.

In another aspect, the present invention provides a method for preparing the virus-like particles comprising transforming a host cell with the expression vector of the present invention and expressing the virus-like particles by culturing the host cell.

The transformed host cell of the present invention may be cultured under batch, fed-batch or continuous fermentation conditions, and since the host cell can express the virus-like particles by transformation, virus-like particle proteins of the present invention can be obtained from the cultured host cell.

At this time, the conventional batch fermentation method can use a closed system. In the closed system, the culture medium is prepared before fermentation is performed, the medium is inoculated with an organism, and fermentation can occur without adding any components to the medium.

In certain cases, the pH and oxygen content rather than the carbon source content of the growth medium, may be varied during the batch method. The metabolites and cellular biomass of the batch system may change until fermentation is stopped. In a batch system, the cells progress from a lag phase to a hypergrowth log phase and finally reach the stationary phase wherein the growth rate decreases or stops. In a typical period, the cells in the log phase can produce most of the proteins.

A variation of the standard batch system is the "fed-batch fermentation" system. In this system, nutrients (e.g., carbon source, nitrogen source, $O_2$, and, typically, other nutrients) can be added when their concentrations in a culture fall below a threshold.

Fed-batch systems may be useful when suppression of catabolic products inhibits the metabolism of cells and it is desirable for the medium to have a limited amount of nutrients. The measurement of the actual nutrient concentration in the fed-batch system can be predicted based on changes in measurable factors such as pH, dissolved oxygen and partial pressure of waste gas such as $CO_2$. Batch and fed-batch fermentations are general systems and are well known in the art.

Continuous fermentation is an open system in which a defined culture medium is continuously added to the bioreactor and the same amount of conditioned medium is removed simultaneously during the process. Continuous fermentation can generally maintain a constant high density culture where the cells are initially in log phase growth. In continuous fermentation, it may be possible to manipulate one factor or any number of factors that affect cell growth or final product concentration.

For example, limiting nutrients such as a carbon source or a nitrogen source can be maintained at a fixed rate, and all other parameters can be properly maintained.

In other systems, many factors affecting growth may change continuously while the cell concentration measured by media turbidity remains constant. Continuous systems try to maintain steady state growth conditions. Thus, the cell loss caused by removal of the medium can be balanced against the rate of cell growth in fermentation. Methods for maintaining nutrients and growth factors during the continuous fermentation process, as well as techniques for maximizing the rate of product formation, are known in the art.

Modifications of the type of each configuration, the introduction ratio, and the like may be applied based on the description of the present invention by those skilled in the art, and if equivalent technical effects are implemented despite the modifications, it will be covered by the technical idea of the present invention.

The present invention is further described through the following examples, but it will be apparent that the present invention is not limited by the following examples.

Example 1: Preparation of Combination Virus-Like Particles (TG1/TG4/TG6 VLP)

Figure 26:
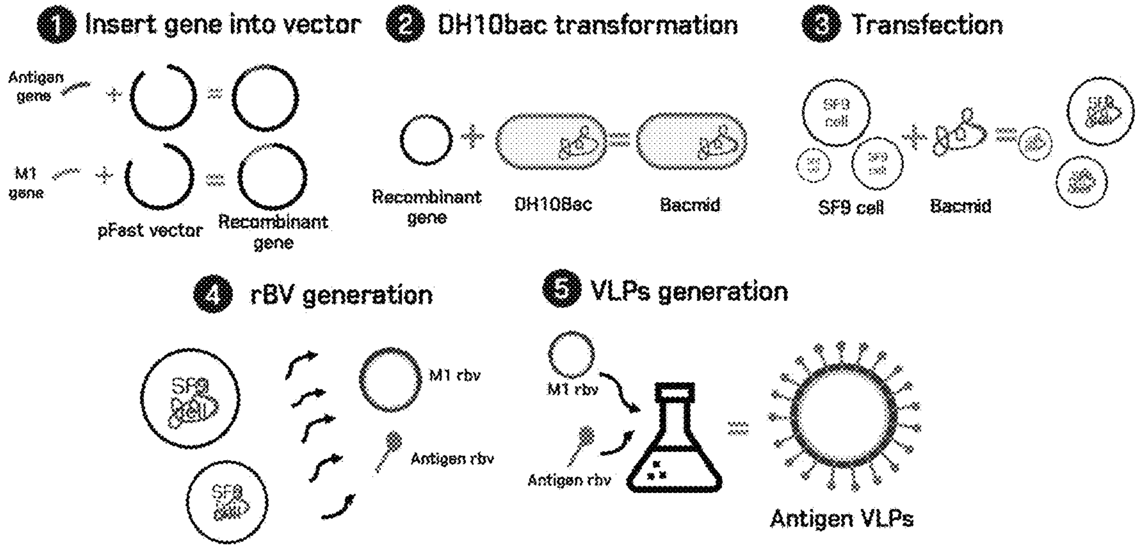
FIG. 26 shows a schematic diagram of a method for generating VLPs.

The gene of influenza virus matrix protein 1 (M1) used in the present example was obtained by transfecting MDCK cells with an influenza virus, crushing the cells to obtain the virus, and amplifying the obtained RNA through PCR using primers. The genes of *Toxoplasma gondii* inner membrane complex (TG1), *Toxoplasma gondii* Rhoptry protein 18 (TG4), and *Toxoplasma gondii* Microneme protein 8 (TG6) were obtained by grinding the RH strain of *Toxoplasma gondii* to obtain RNA and amplifying the RNA through PCR using primers. In order to generate TG1 VLP, TG4 VLP and TG6 VLP, as shown in FIG. 26, these obtained genes were inserted into a pFastBac vector, respectively, the vectors were cloned into DH5a cells, and the obtained genes were then cloned into the DH10Bac vector again. The gene of the DH10Bac vector was inserted into a SF9 cell, an insect cell, to obtain a protein of the desired gene antigen.

The gene of *Toxoplasma gondii* inner membrane complex (TG1) was amplified through PCR using a forward primer (5'-AAAGAATTCACCATGGGGAACACGGCGTGCTG-3') and a reverse primer (5'-TTACTCGAGTTAGTTTCTGTCGTTGCTTGC-3').

The gene of *Toxoplasma gondii* Rhoptry protein 18 (TG4) was amplified through PCR using a forward primer (5'-CGGGATCCATGTTTTCGGTACAGCGGCCA-3') and a reverse primer (5'-GCGTCGACTTATTCTGTGTGGAGATGTTCCTG-3').

The gene of *Toxoplasma gondii* Microneme protein 8 (TG6) was amplified through PCR using a forward primer (5'-AAAGAATTCACCATGAAGGCCAATCGAATATG-3') and a reverse primer (5'-TTACTCCAGTTAGGACCAGATACCGCCCGA-3').

The gene of influenza matrix protein 1 (M1) was amplified through RT-PCR using a forward primer (5'-AAAGAATTCACCATGAGTCTTCTAACCGAGGT-3') and a reverse primer (5'-TTACTCGAGTTACTCTAGCTCTATGTTGAC-3').

i) Preparation of TG1 VLP

The IMC (TG1) gene and the M1 gene were inserted into the pFastBac vector having restriction enzyme sites (EcoR I and Xho I), respectively. The insertion of the IMC gene (TG1) or the M1 gene into the pFastBac vector was confirmed by cutting the vector with EcoR I and Xho I restriction enzymes.

The nucleic acid sequences of the inserted genes were confirmed to be identical to the known sequences (IMC: HQ012579, M1: EF467824) by DNA sequencing (Eurofins MWG Operon).

Subsequently, in order to prepare a recombinant baculovirus (rBV) expressing TG1 and a recombinant baculovirus (rBV) expressing M1, each pFastBac vector was transformed using white/blue screening, and the DNA was transfected into SF9 cells using cellfectin II (Invitrogen, Carlsbad, Calif., USA), and recombinant baculoviruses (rBVs) were prepared according to the manufacturer's manual with the Bac-to-Bac expression system (Invitrogen).

TG1 VLPs were produced in SF9 insect cells co-infected with the recombinant rBV expressing TG1 and the recombinant rBV expressing M1. The SF9 cell culture supernatant was harvested at 3 days after infection, and then the cells were removed by centrifugation at 4° C. for 30 minutes at 6000 rpm. VLPs in the supernatant were purified and pelleted.

TG1 VLPs were resuspended overnight in phosphate-buffered saline (PBS) at 4° C., harvested for 1 hour at 4° C., 45,000×g through a discontinuous sucrose gradient (20-30-60%), and purified. Protein concentration was determined by QuantiPro BCA Assay Kit (Sigma-Aldrich).

ii) Preparation of TG4 VLP

Except that the ROP18 (TG4) gene instead of the IMC (TG1) gene was inserted into the pFastBac vector having restriction enzyme sites (BamHI and XbaI) to prepare a recombinant rBV expressing TG4, TG4 VLPs were prepared in SF9 insect cells co-infected with the recombinant rBV expressing TG4 and the recombinant rBV expressing M1 in the same manner as TG1 VLP. At this time, the insertion of the ROP18 (TG4) gene into the pFastBac vector was confirmed by cutting the vector with BamHI and XbaI restriction enzymes.

The nucleic acid sequences of the inserted genes were confirmed to be identical to the known sequences (ROP18: AM075204, M1: EF467824) by DNA sequencing (Eurofins MWG Operon).

iii) Preparation of TG6 VLP

Except that the MIC8 (TG6) gene instead of the IMC (TG1) gene was inserted into the pFastBac vector having restriction enzyme sites (EcoR I and Xho I) to prepare a recombinant rBV expressing TG6, TG6 VLPs were prepared in SF9 insect cells co-infected with the recombinant rBV expressing TG6 and the recombinant rBV expressing M1 in the same manner as TG1 VLP. At this time, the insertion of the MIC8 (TG6) gene into the pFastBac vector was confirmed by cutting the vector with EcoR I and Xho I restriction enzymes.

The nucleic acid sequences of the inserted genes were confirmed to be identical to the known sequences (MIC8: AF353165, M1: EF467824) by DNA sequencing (Eurofins MWG Operon).

iv) Preparation of Combination Virus-Like Particles (TG1/TG4/TG6 VLP)

A combination virus-like particle (TG1/TG4/TG6 VLP) was generated by combining each of the prepared TG1 VLP, TG4 VLP and TG6 VLP in a ratio of 1:1:1.

Example 2: Preparation of Multi-Antigen Virus-Like Particles (TG146 VLP)

Multi-antigen virus-like particles (TG146 VLPs) were prepared by co-infection of SF9 insect cells with the recombinant rBVs expressing TG1, TG4, TG6 and M1, respectively, prepared in Example 1. The infected SF9 cell culture supernatant was harvested and pelleted in the same manner as the method for preparing TG1 VLP to prepare TG146 VLPs expressing TG1, TG4 and TG6 simultaneously.

VLPs prepared in Examples 1 and 2 are as follows.

TABLE 1

| Example | Name | Abbreviation | Surface antigen protein contained in VLP |
|---|---|---|---|
| 1 | Combination virus-like particle | TG1/TG4/TG6 VLP | IMC, ROP18, or MIC8 |
| 2 | Multi-antigen virus-like particle | TG146 VLP | IMC, ROP18, and MIC8 |

Experimental Example 1: Characterization of Virus-Like Particles

Multi-antigen virus-like particles (TG146 VLPs) and combination virus-like particles (TG1/TG4/TG6 VLPs) were confirmed by western blot and electron microscopy. TG1 VLP, TG4 VLP, TG6 VLP and TG146 VLP at concentrations of 27 μg, 9 μg, and 3 μg were loaded in each lane for SDS-PAGE and visualized by western blot. Anti-*Toxoplasma gondii* polyclonal antibodies and anti-M1 monoclonal antibodies (Abcam, Cambridge, UK) were used as probes to detect TG1, TG4, TG6 and M1 proteins by western blot. Anti-*Toxoplasma gondii* polyclonal antibodies were obtained from BALB/c mice infected with *Toxoplasma gondii* ME49.

Figure 1C:
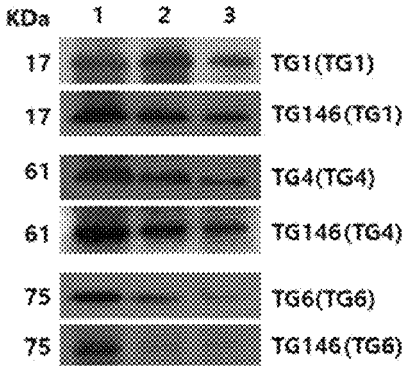
Figure 1D:
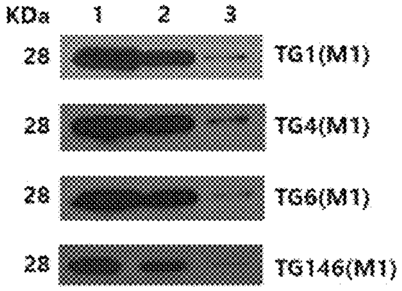
Figure 2A:
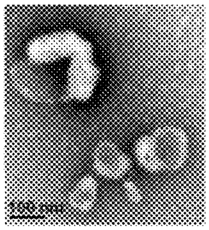
FIGS. 2A-2D show the transmission electron microscopy (TEM) of TG1 VLP, TG4 VLP, TG6 VLP, and TG146 VLP: (A) TG1 VLP; (B) TG4 VLP; (C) TG6 VLP; (D) TG146 VLP.
Figure 2B:
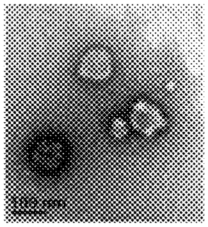
Figure 2C:
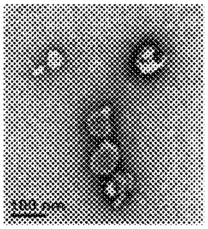
Figure 2D:
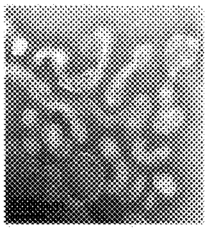

As a result, TG1 protein (17 KDa) contained in TG1 VLP and TG146 VLP, TG4 protein (61 KDa) contained in TG4 VLP and TG146 VLP, and TG6 protein (75 KDa) contained in TG6 VLP and TG146 VLP were confirmed (FIG. 1C), and the M1 protein (28 KDa) contained in each VLP was confirmed (FIG. 1D).

For size measurement, TG1 VLP, TG4 VLP, TG6 VLP and TG146 VLP were negatively stained and observed with a transmission electron microscope (TEM) (JEOL 2100, JEOL USA, Inc.; Peabody, Mass., USA).

Each VLP had spikes formed on the surface when observed by an electron microscope, and its size was about 40 to 120 nm (FIG. 2).

Experimental Example 2: Protective Immunity Test of *Toxoplasma gondii* VLPs in an Animal Model 2-1. Preparation of an Animal Model 7-week-old BALB/c female mice were randomly divided into different experimental groups (20 per group) to receive TG146 VLP or TG1/TG4/TG6 VLP. At weeks 0 and 4, 60 μg of TG146 VLP, and total 60 μg of TG1/TG4/TG6 VLP which is combination of 20 μg of each of TG1 VLP, TG4 VLP, and TG6 VLP were used for intranasal (IN) immunization of mice from each group. At 4 weeks after the $2^{nd}$ immunization, mice were challenged with $1\times10^3$ tachyzoites of *Toxoplasma gondii* (GT1) by intraperitoneal (IP) injection. Ten mice from each group were sacrificed at 7 days after challenge and ascites of abdominal cavity and spleen samples were collected. Living ten mice in each group were observed daily to monitor body weight change and survival rate until death.

2-2. Test of *Toxoplasma gondii*-Specific Antibody Response and Antibody Neutralizing Activity At 4 weeks after the $1^{st}$ (prime) and the 2nd (boost) immunizations, mouse sera were collected from all groups. Sera of naive mice were used as a negative control, and sera of mice infected with *Toxoplasma gondii* (ME49) were used as a positive control. *Toxoplasma gondii*-specific IgG antibodies were analyzed by enzyme-linked immunosorbent assay (ELISA). A 96-well flat bottom immunoplate was coated with 100 μL of *Toxoplasma gondii* antigen at a final concentration of 0.5 μg/mL in 0.05 M carbonate-bicarbonate buffer (pH 9.6) per well at 4° C. overnight. Then, 100 μL of serum samples (diluted 1:100 in Phosphate Buffered Saline with Tween 20 (PBST)) per well were incubated in the plate for 2 hours at 37° C. as the primary antibody response. HRP-conjugated goat anti-mouse IgG in PBST (100 μL/well, diluted 1:2,000 in PBST) was used to determine the *Toxoplasma gondii*-specific IgG response.

Meanwhile, mice sera were collected at 4 weeks after the 2nd immunization, and complement was inactivated at 56° C. for 30 minutes. Then, 50 μL of the sera from the immunization was incubated with 100 tachyzoites of *Toxoplasma gondii* (GT1) at 37° C. for 1 hour. Naïve mice (10 mice in each group) were intraperitoneally (IP) infected with a mixture of tachyzoites and serum. A mixture of tachyzoites and PBS was used as a control. At 7 days after infection, tachyzoites of *Toxoplasma gondii* were collected from the abdominal cavities of the mice and counted with a hemocytometer chamber under a microscope.

Figure 3A:
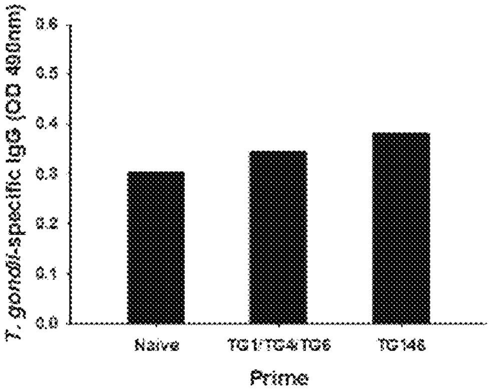
FIGS. 3A-3C show the levels of *Toxoplasma gondii*-specific antibody response in sera of a negative control (Naïve), TG1/TG4/TG6 VLP injection group (TG1/TG4/TG6), and TG146 VLP injection group (TG146) and the levels of parasite neutralizing activity in each group after $1^{st}$ (prime) and $2^{nd}$ (boost) immunizations: (A) IgG levels after $1^{st}$ immunization; (B) IgG levels after $2^{nd}$ immunization; (C) Parasite neutralizing activities.
Figure 3B:
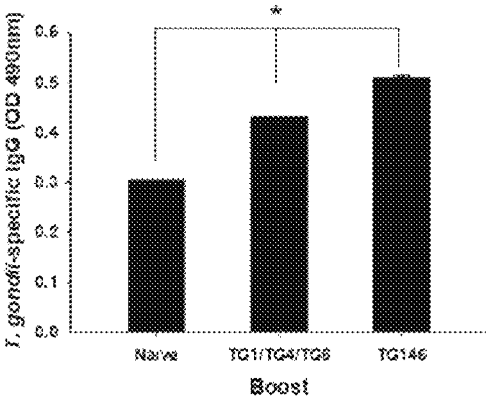
Figure 3C:
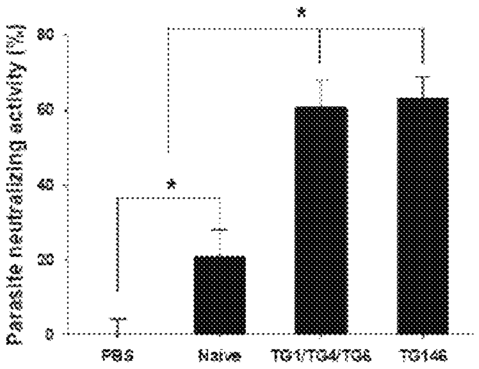

As a result, as shown in FIG. 3, it was found that the *Toxoplasma gondii*-specific IgG antibody was induced after the $1^{st}$ immunization (FIG. 3A) and the $2^{nd}$ immunization (FIG. 3B). In particular, it was found that the multi-antigen VLP (TG146) group had a significantly higher level of *Toxoplasma gondii*-specific IgG antibody response after the $2^{nd}$ immunization compared to the combination VLP (TG1/TG4/TG6) group (* $P<0.05$). In addition, as a result of evaluating the serum neutralizing activity using the sera of the VLP immunized mice, the sera of both the multi-antigen VLP (TG146) group and the combination VLP (TG1/TG4/TG6) group significantly inhibited *Toxoplasma gondii* (GT1) replication compared to the sera of the PBS control and the naive mice (FIG. 3C, * $P<0.05$).

2-3. Test of Immune Cell Response

The distribution of T cells ($CD4^+$ and $CD8^+$) and germinal center B cells (GC) from spleen cells of mice at 7 days after challenge infection was analyzed by flow cytometry. Briefly, $1\times10^6$ splenocytes (each tube) in staining buffer (2% bovine serum albumin and 0.1% sodium azide in 0.1 M PBS) were incubated with Fc Block (clone 2.4G2; BD Biosciences, CA, USA) at 4° C. for 15 minutes. For surface staining, cells were incubated with surface antibodies (CD3e-PE-Cy5, CD4-FITC, CD8a-PE, B220-FITC, GL7-PE; BD Biosciences, CA, USA) for 30 minutes at 4° C. Splenocytes were washed with staining buffer and fixed with 4% paraformaldehyde for 30 min at 4° C. prior to acquisition using a BD Accuri C6 flow cytometer (BD Biosciences, CA, USA). Data were analyzed using C6 analysis software (BD Biosciences, CA, USA).

Figure 4:
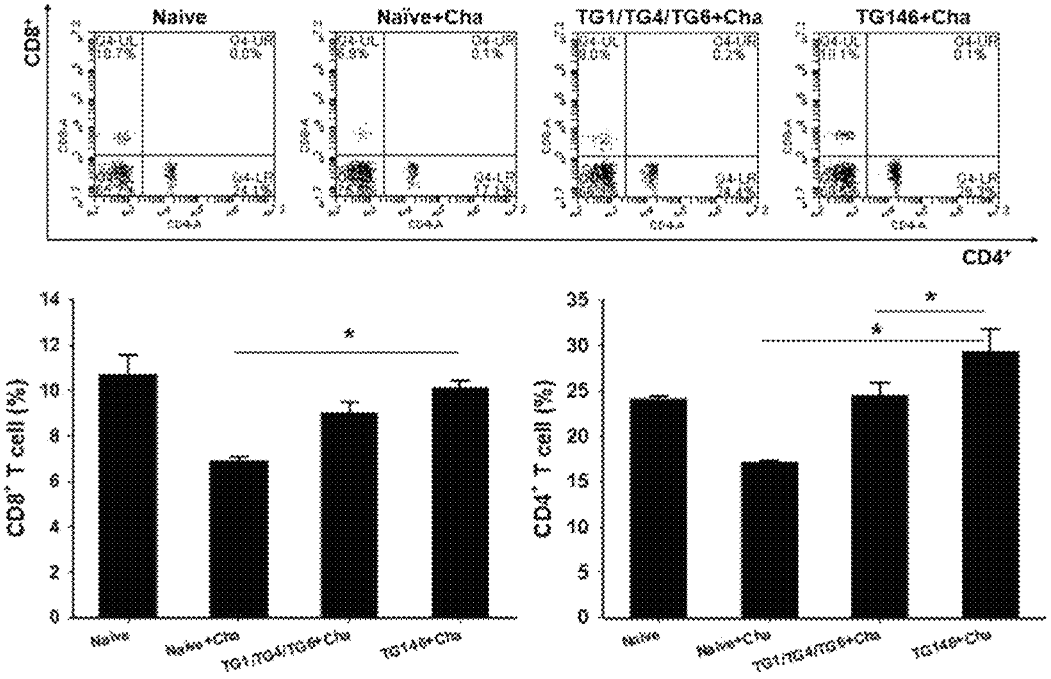
FIG. 4 shows the results of flow cytometry of distribution of T cells ($CD4^+$ and $CD8^+$) from spleen cells of mice after challenge infection of a negative control (Naïve), a positive control (Naïve+Cha), TG1/TG4/TG6 VLP injection group (TG1/TG4/TG6+Cha), and TG146 VLP injection group (TG146+Cha).
Figure 5:
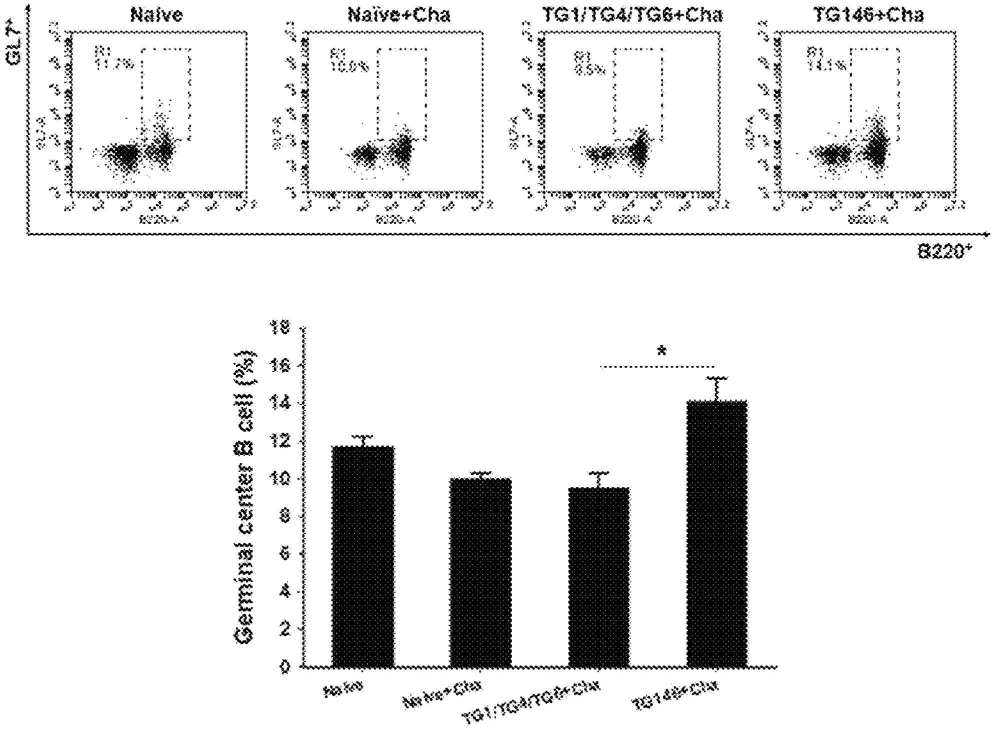
FIG. 5 shows the results of flow cytometry of distribution of germinal center B cells (GC) from spleen cells of mice after challenge infection of a negative control (Naïve), a positive control (Naïve+Cha), TG1/TG4/TG6 VLP injection group (TG1/TG4/TG6+Cha), and TG146 VLP injection group (TG146+Cha).

As a result, as shown in FIGS. 4 and 5, at 7 days after challenge, significantly high levels of $CD4^+$ T cells and $CD8^+$ T cells were found in the group immunized with multi-antigen VLP (TG146+Cha) or the group immunized with combination VLP (TG1/TG4/TG6+Cha) compared to the positive control group (Naïve+Cha) (FIG. 4, * P<0.05). In particular, significantly high levels of $CD4^+$ T cell response were found in the group immunized with multi-antigen VLP (TG146+Cha) compared to the group immunized with combination VLP (TG1/TG4/TG6+Cha) (* P<0.05). In addition, the group immunized with multi-antigen VLP (TG146+Cha) showed significantly higher levels of germinal center B cell responses compared to the group immunized with combination VLP (TG1/TG4/TG6+Cha) (FIG. 5, * P<0.05). From this, a remarkably good immune response level of a virus-like particle vaccine simultaneously expressing TG1, TG4 and TG6 was confirmed.

2-4. Apoptosis Analysis

To analyze the apoptosis of splenocytes, Annexin-V and PI were stained using BD Apoptosis Detection Kit I (BD Biosciences, CA, USA). Splenocytes were collected at 7 days after challenge. Then, $1 \times 10^5$ cells in binding buffer were centrifuged at 400×g for 10 minutes and the supernatant was discarded. Cells were stained with 5 μl Annexin V-FITC and PI for 15 minutes at room temperature in the dark. The number of apoptotic cells was determined with a BD Accuri C6 Flow Cytometer (BD Biosciences, CA, USA) and analyzed with C6 Analysis Software (BD Biosciences, CA, USA).

As a result, as shown in FIG. 6, a significantly higher level of apoptosis response was found in the non-immunized positive control (Naïve+Cha), whereas a significantly low level of apoptosis response was found in the group immunized with multi-antigen VLP (TG146+Cha) or the group immunized with combination VLP (TG1/TG4/TG6+Cha). In particular, compared to the group immunized with the combination VLP (TG1/TG4/TG6+Cha), the group immunized with the multi-antigen VLP (TG146+Cha) showed significantly lower levels of apoptosis response (* P<0.05).

2-5. Test of Survival Rate, Body Weight Change and Parasite Load for Challenge Infection with *Toxoplasma gondii*

As described above, in order to determine the protective efficacy of the VLP vaccine, immunized mice and control mice were intraperitoneally challenged (IP) with lethal *Toxoplasma gondii* GT1 strain ($1 \times 10^3$ tachyzoites) at 4 weeks after the $2^{nd}$ immunization. In addition, in order to assess the efficacy of the VLP vaccine, tachyzoites of *Toxoplasma gondii* were collected from the abdominal cavities of mice at 7 days after challenge infection and counted.

As a result, as shown in FIG. 7, while some mice in the group immunized with multi-antigen VLP (TG146+Cha) survived until day 14, all mice in other groups (Naïve+Cha, TG1/TG4/TG6+Cha) died within 14 days after challenge (FIG. 7A). In addition, mice immunized with multi-antigen VLP (TG146+Cha) showed only 10.5% body weight loss on day 11, whereas mice immunized with combination VLP (TG1/TG4/TG6+Cha) showed 21.5% body weight loss on day 13 and positive control mice (Naïve+Cha) showed 16.8% body weight loss on day 9 (FIG. 7B). Finally, mice immunized with multi-antigen VLP (TG146+Cha) or mice immunized with combination VLP (TG1/TG4/TG6+Cha) significantly inhibited parasite replication compared to the non-immunized positive control (Naïve+Cha) (FIG. 7C, * P<0.05). In particular, TG146+Cha showed significantly higher inhibition of parasite replication compared to TG1/TG4/TG6+Cha (* P<0.05). From this, it can be seen that immunization of mice with TG146 VLP can suppress toxoplasmosis more effectively.

Figure 8:
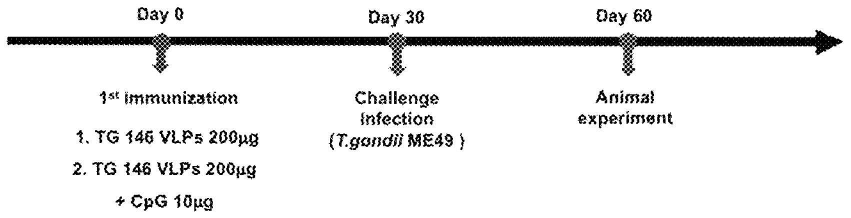
FIG. 8 shows a schematic diagram of a single immunization animal experiment for the co-administration of *Toxoplasma gondii* VLP and CpG.

Experimental Example 3: Test of Combined Administration of *Toxoplasma gondii* VLPs and CpG in an Animal Model 3-1. Single Immunized Animal Experiment 3-1-1. Preparation of an Animal Model As shown in FIG. 8, 7-week-old BALB/c female mice were randomly divided into different experimental groups (6 per group) and administered intramuscularly (IM) or intranasally (IN) with 200 μg of TG146VLP or 200 μg of TG146 VLP+10 μg of adjuvant CpG at day 0 ($1^{st}$ immunization). At 30 days after the $1^{st}$ immunization, mice were challenged via oral route with lethal doses of *Toxoplasma gondii* ME49 450 cysts. Three mice in each group were sacrificed at 30 days after challenge, and brain, spleen and mesenteric lymph nodes (MLN) were isolated. Immune cell activity was determined, and antibody responses in serum, inflammatory responses in the brain, and the size and count of the cysts detected in the brain were determined. Three living mice in each group were monitored for body weight change and survival rate.

3-1-2. Test of *Toxoplasma gondii*-Specific Antibody Response

The sera of mice were collected at 30 days after the challenge infection, and were used to determine the levels of IgG and IgA by ELISA in the same manner as in Experimental Example 2-2.

Figure 9:
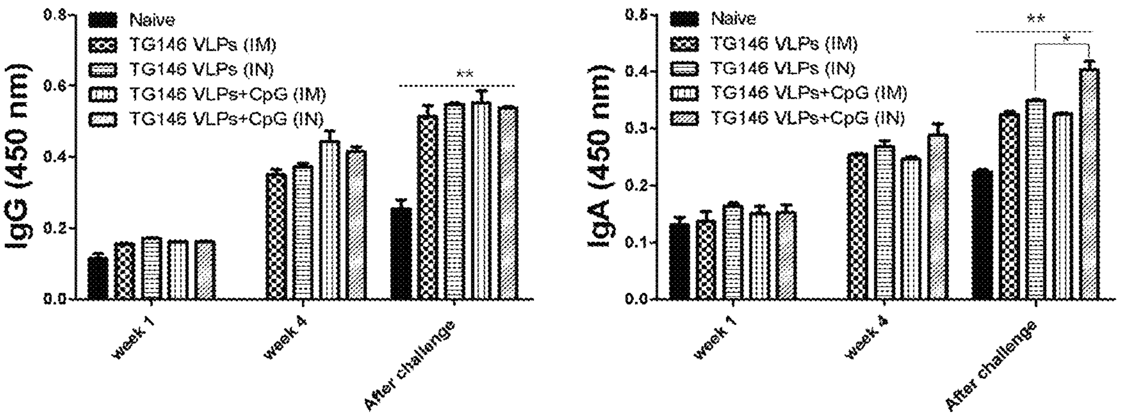
FIG. 9 shows the levels of *Toxoplasma gondii*-specific IgG and IgA in serum at 1 week (week 1) and 4 weeks (week 4) after immunization and after challenge infection of a negative control (Naïve), a group injected with TG146 VLP by IM route (TG146 VLPs (IM)), a group injected with TG146 VLP by IN route (TG146 VLPs (IN)), a group injected with TG146 VLP and CpG by IM route (TG146 VLPs+CpG (IM)), and a group injected with TG146 VLP and CpG by IN route (TG146 VLPs+CpG (IN)) in the single immunization animal experiment.

As a result, as shown in FIG. 9, the group administered with TG146 VLP (TG146 VLPs) and the group administered with TG146 VLP and CpG (TG146 VLPs+CpG) in both the IN immunization and the IM immunization showed significantly higher antibody response levels compared to the non-immunized negative control (Naïve). In particular, the IN immunization induced higher levels of serum IgA compared to the IM immunization (* P<0.05, ** P<0.01).

3-1-3. Test of Immune Cell Response

The activities of $CD4^+$ T cells, $CD8^+$ T cells, germinal center B cells and B cells in the spleen and mesenteric lymph nodes (MLN) of mice isolated at 30 days after challenge infection were analyzed in the same manner as in Experimental Example 2-3.

Figure 10:
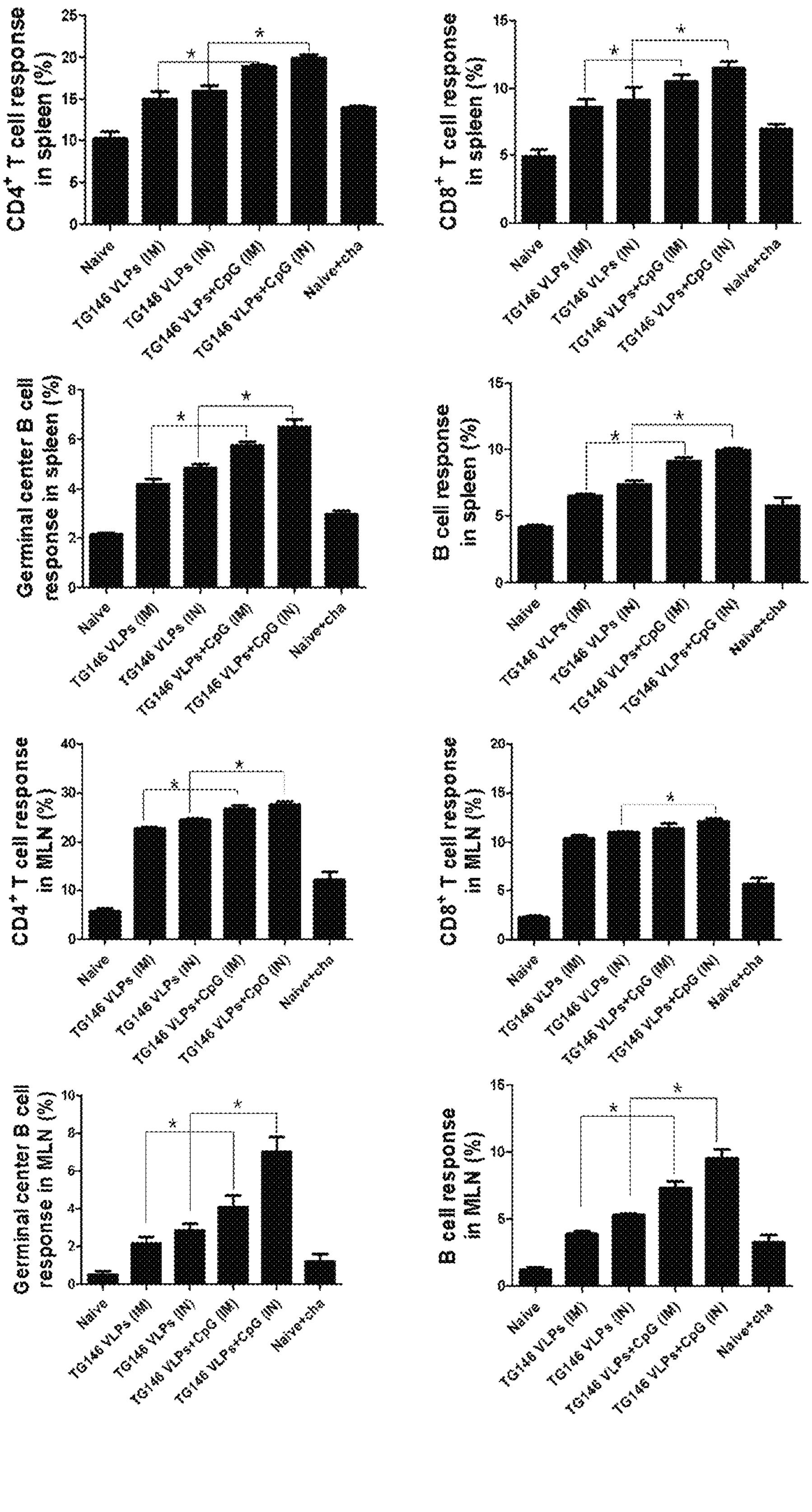
FIG. 10 shows the results of flow cytometry of the spleen and mesenteric lymph node (MLN) after challenge infection of each group in the single immunization animal experiment.

As a result, as shown in FIG. 10, at 30 days after challenge, the levels of $CD4^+$ T cells, $CD8^+$ T cells, germinal center B cells and B cells in spleen and MLN of the TG146 VLPs+CpG group were significantly higher than the TG146 VLP group for IN immunization. For the IM immunization, the levels of $CD4^+$ T cells, $CD8^+$ T cells, germinal center B cells and B cells in the spleen, and the levels of $CD4^+$ T cells, germinal center B cells and B cells in the MLN were significantly higher (* P<0.05). In particular, the IN immunization induced higher levels of $CD4^+$ T cells, $CD8^+$ T cells, germinal center B cells and B cell responses in the spleen and the MLN compared to the IM immunization.

3-1-4. Test of Inflammatory Response

To determine the extent to which the inflammatory response is suppressed after infection of immunized mice, the brains of mice isolated at 30 days after challenge were crushed and centrifuged for 5 minutes at 10000 RPM. And then the concentrations of inflammatory cytokines (IFN-γ and IL-6) in the supernatant were determined using ELISA kit (BD Biosciences, San Jose, Calif., USA) according to the manufacturer's instructions.

Figure 11:
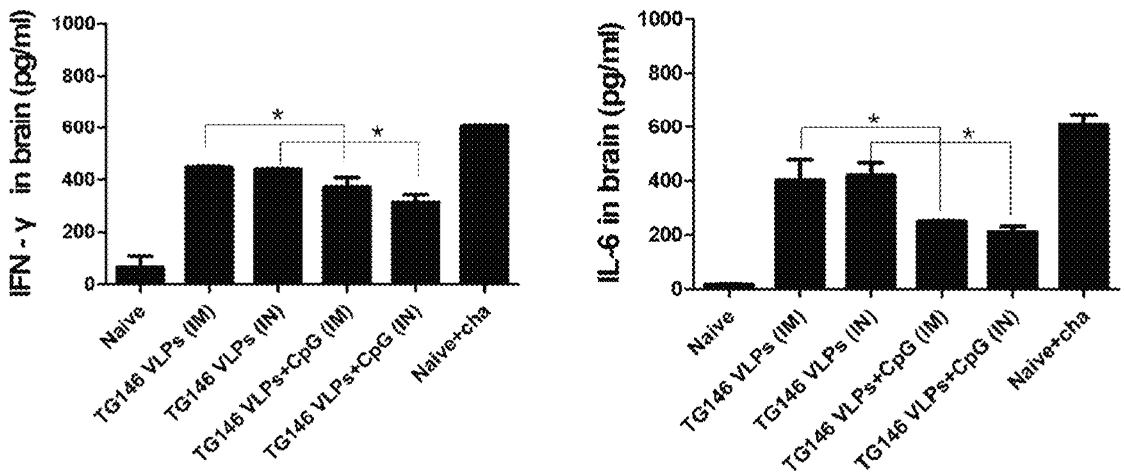
FIG. 11 shows the levels of inflammatory cytokines after challenge infection of each group in the single immunization animal experiment.

As a result, as shown in FIG. 11, while the positive control (Naïve+cha) showed high levels of inflammatory cytokines IFN-γ and IL-6 and thus the induction of a high inflammatory response in the brain, low levels of IFN-γ and IL-6 were measured in the brain cells of mice immunized with TG146 VLP and TG146 VLP+CpG in both the IM immunizations and the IN immunization. Among them, the group immunized with TG146 VLP+CpG showed significantly lower levels of IFN-γ and IL-6 than the group immunized with TG146 VLP (* P<0.05).

3-1-5. Test of the Size and Count of Cysts in the Brain Following Infection

Mice brains isolated at 30 days after challenge were crushed, and brain tissues were harvested and homogenized in 400 μl PBS with a syringe. The homogenized solution was resuspended in 45% Percoll, and then centrifuged at 4° C. and 12100 RPM for 20 minutes. Then, the cyst layer was carefully collected and washed with PBS at 6000 RPM for 20 minutes. 5 μl of the collected cysts was counted 5 times in 5 regions under a microscope (Leica DMi8, Leica, Wetzlar, Germany).

Figure 12:
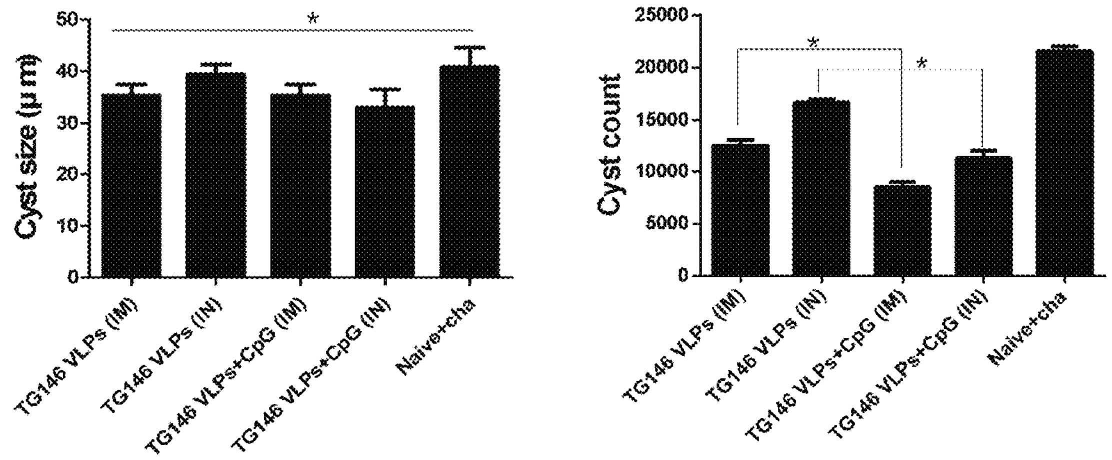
FIG. 12 shows the sizes and counts of cysts in brain tissues after challenge infection of each group in the single immunization animal experiment.

As a result, as shown in FIG. 12, the cyst size was the smallest when intranasally immunized with TG146 VLP+CpG. Further, when immunized with TG146 VLP or TG146 VLP+CpG, the counts of cysts from the IN immunization and the IM immunization were significantly reduced. Particularly, the group immunized with TG146 VLP+CpG showed significantly fewer cysts than the group immunized with TG146 VLP (* P<0.05).

3-1-6. Test of Survival Rate and Body Weight Change Following Infection

At 30 days after VLP inoculation, mice were challenged with *Toxoplasma gondii* ME49 and the survival rates and the body weight changes of mice in each group were determined for 35 days.

Figure 13:
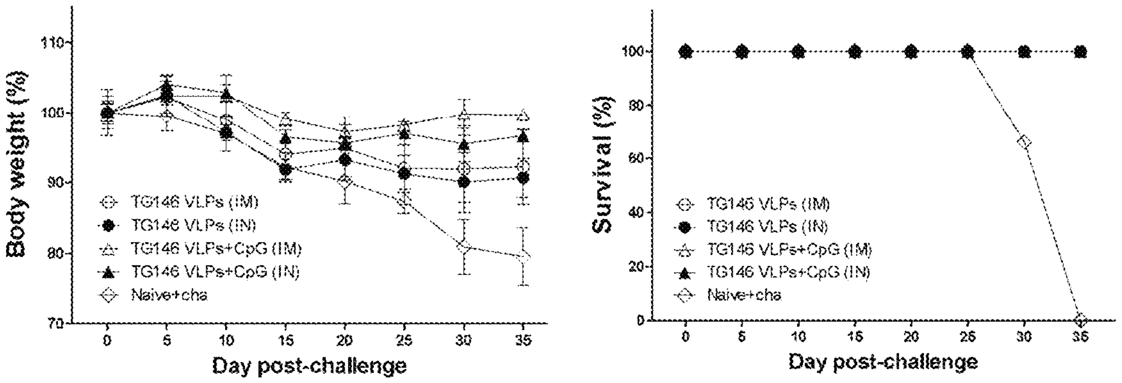
FIG. 13 shows the body weight changes and survival rates after challenge infection of each group in the single immunization animal experiment.

As a result, as shown in FIG. 13, all mice in the positive control group (Naïve+Cha) died at 35 days after infection, but all mice in the IN immunization group or the IM immunization group (TG146 VLP and TG146 VLP+CpG) survived. In addition, the lowest weight loss rate was observed when immunized intranasally with TG146 VLP+CpG.

3-2. Double Immunized Animal Experiment 3-2-1. Preparation of an Animal Model

Figure 14:
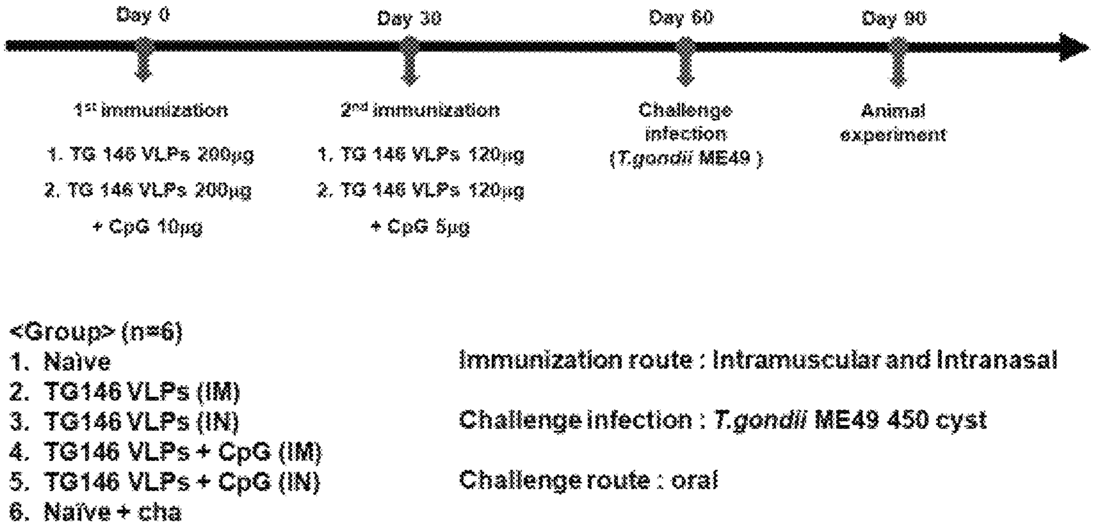
FIG. 14 shows a schematic diagram of a double immunization animal experiment for the co-administration of *Toxoplasma gondii* VLP and CpG.

As shown in FIG. 14, mice inoculated with 200 μg of TG146VLP or 200 μg of TG146 VLP+10 μg of CpG by IM or IN route of Experimental Example 3-1 were administered with 120 μg of TG146VLP or 120 μg of TG146 VLP+5 μg of CpG by the same route at 30 days after the 1$^{st}$ immunization (2$^{nd}$ immunization). At 30 days after the 2$^{nd}$ immunization, the mice were challenged with a lethal dose of *Toxoplasma gondii* ME49 450 cysts via oral route, and then sacrificed at 30 days after infection when the degree of infection maximized. Then, brain, spleen and mesenteric lymph nodes (MLN) were isolated, and the activity of the immune cells, the antibody response in serum, the inflammatory response in the brain, and the size and count of cysts detected in the brain were determined. Living mice in each group were monitored for body weight change and survival rate.

3-2-2. Test of *Toxoplasma gondii*-Specific Antibody Response

As in the single immunization animal experiment, the IgG and IgA antibody responses in the sera of mice obtained at 30 days after the 1$^{st}$ and the 2$^{nd}$ immunizations and challenge infection were determined.

Figure 15:
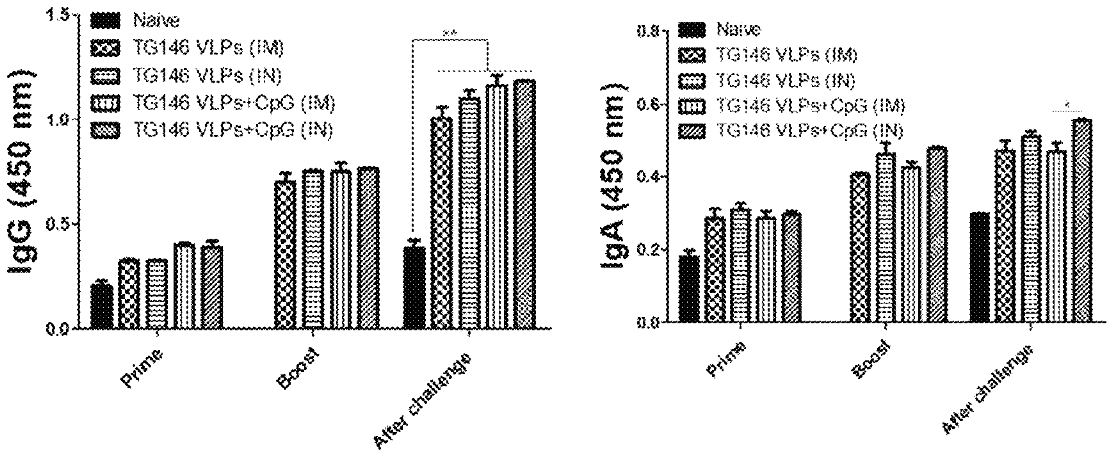
FIG. 15 shows the levels of *Toxoplasma gondii*-specific IgG and IgA in serum after $1^{st}$ (prime) and $2^{nd}$ (boost) immunization and challenge infection of a negative control (Naïve), a group injected with TG146 VLP by IM route (TG146 VLPs (IM)), a group injected with TG146 VLP by IN route (TG146 VLPs (IN)), a group injected with TG146 VLP and CpG by IM route (TG146 VLPs+CpG (IM)), and a group injected with TG146 VLP and CpG by IN route (TG146 VLPs+CpG (IN)) in the double immunization animal experiment.

As a result, as shown in FIG. 15, the antibody response level after challenge infection was significantly higher in the mouse group in which CpG was additionally inoculated, and particularly, the IN immunization induced higher level of serum IgA than the IM immunization. (* P<0.05, ** P<0.01).

3-2-3. Test of Immune Cell Response

As in the single immunization animal experiment, the activities of CD4$^+$ T cells, CD8$^+$ T cells, germinal center B cells and B cells in the spleen and mesenteric lymph nodes (MLN) of mice isolated at 30 days after challenge infection were analyzed.

Figure 16:
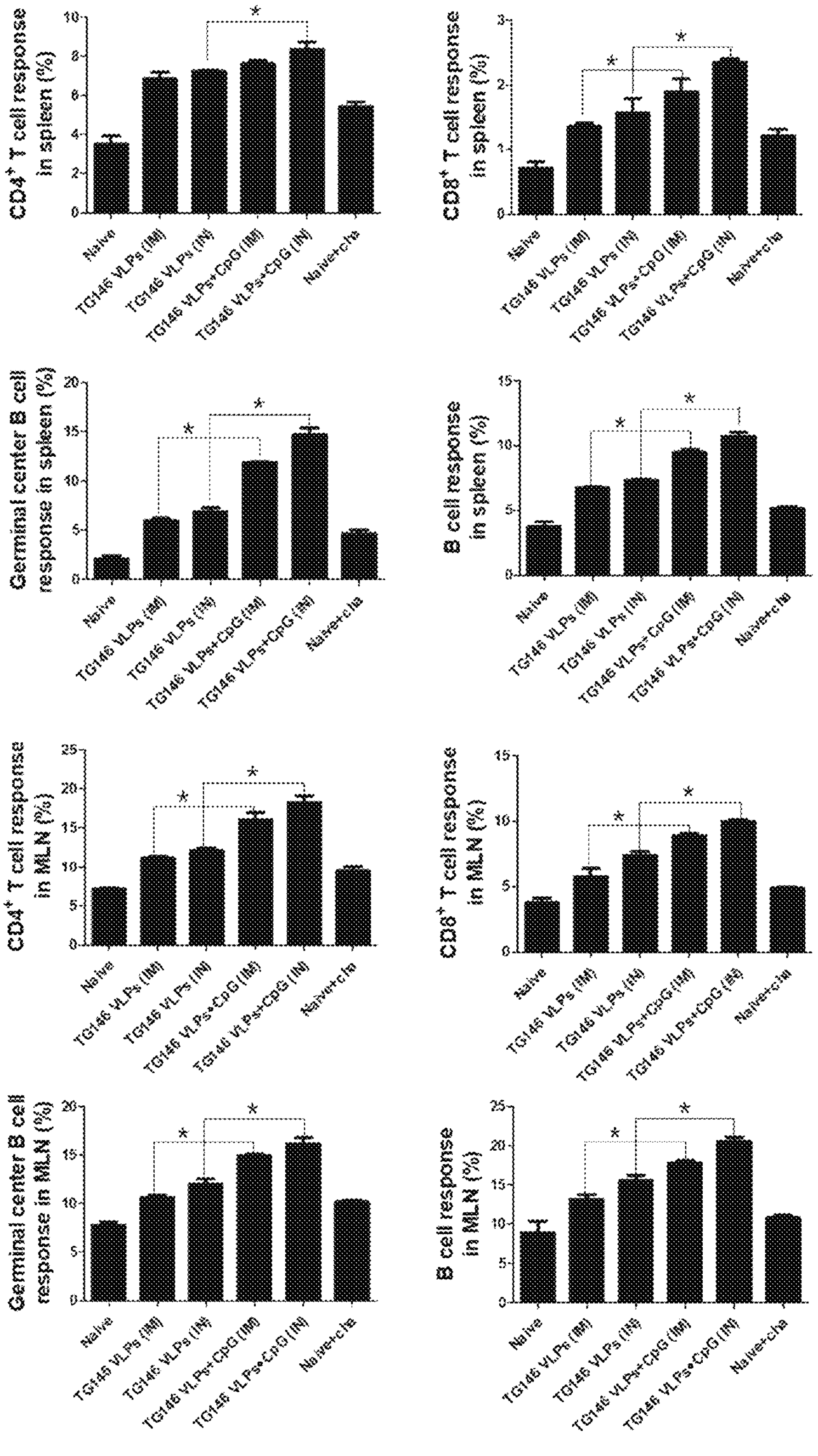
FIG. 16 shows the results of flow cytometry of the spleen and mesenteric lymph node (MLN) after challenge infection of each group in the double immunization animal experiment.

As a result, as shown in FIG. 16, at 30 days after challenge, the levels of CD4$^+$ T cells, CD8$^+$ T cells, germinal center B cells and B cells in spleen and MLN of the immunization groups (TG146 VLP and TG146 VLP+CpG) were significantly higher than the positive control (Naïve+Cha) in both the IN immunization and the IM immunization (* P<0.05). In particular, the IN immunization induced higher level of immune cell response than the IM immunization and the mesenteric lymph node (MLN) showed a higher level of immune cell activity than the spleen.

3-2-4. Test of Inflammatory Response

As in the single immunization animal experiment, the inflammatory response was determined in the brains of mice isolated at 30 days after challenge, and the levels of inflammatory cytokines IFN-γ and IL-6, which are indicators of the inflammatory response, were analyzed and compared between groups.

Figure 17:
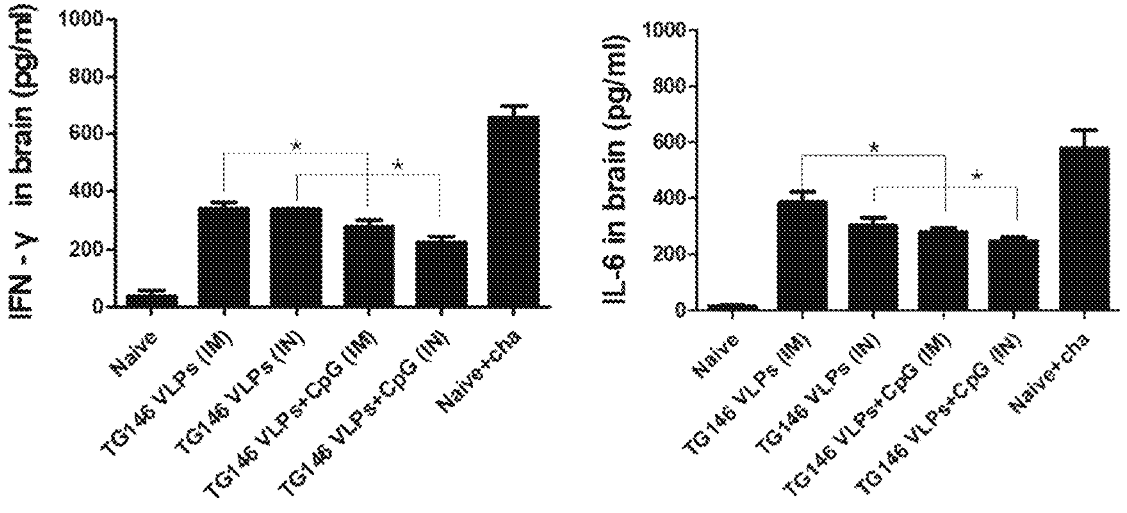
FIG. 17 shows the levels of inflammatory cytokines after challenge infection of each group in the double immunization animal experiment.

As a result, as shown in FIG. 17, the levels of inflammatory cytokines IFN-γ and IL-6 were the highest in the positive control group (Naïve+cha), and other immunization groups (TG146 VLP and TG146 VLP+CpG) showed significantly lower levels of IFN-γ and IL-6 in both the IN immunization and the IM immunization. Particularly, the group of mice further inoculated with CpG showed a lower level of IFN-γ and IL-6 than the group of mice in which CpG was not inoculated (* P<0.05).

3-2-5. Test of the Size and Count of Cysts in the Brain Following Infection

As in the single immunization animal experiment, the size and count of cysts collected from the brains of mice isolated at 30 days after challenge was determined.

Figure 18:
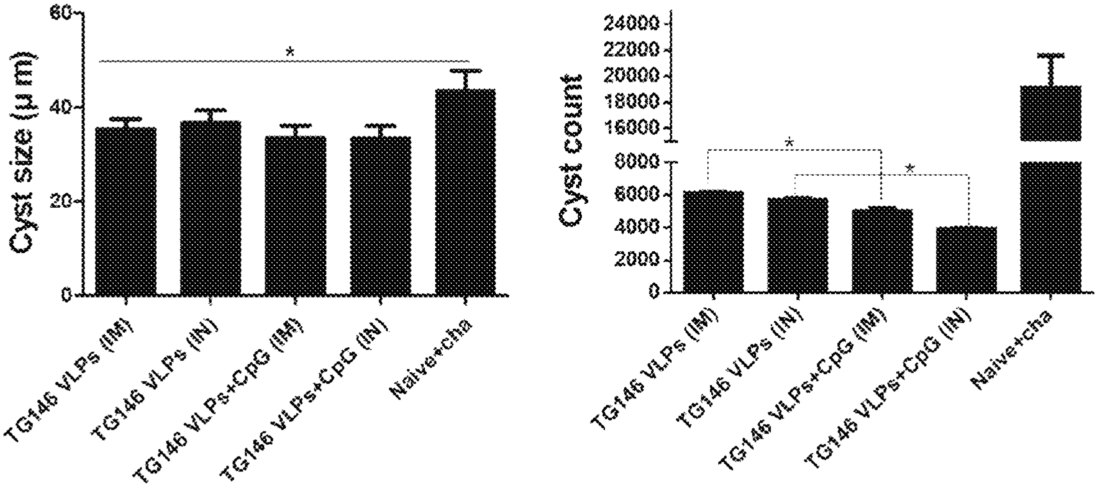
FIG. 18 shows the sizes and counts of cysts in brain tissues after challenge infection of each group in the double immunization animal experiment.

As a result, as shown in FIG. 18, the positive control group (Naïve+cha) showed a large number of cysts with a significant difference compared to the IN immunization group or the IM immunization group (TG146 VLP and TG146 VLP+CpG). Among the immunization groups, the count of cysts was the lowest when immunized with TG146 VLP+CpG intranasally. The difference in the size of the cysts between the immunization groups was not large, but the cyst size in TG146 VLP+CpG (IN) was the smallest compared to Naïve+cha (* P<0.05).

3-2-6. Test of Survival Rate and Body Weight Change Following Infection

As in the single immunization animal experiment, survival rates and body weight changes of mice in each group were measured for 35 days after challenge.

Figure 19:
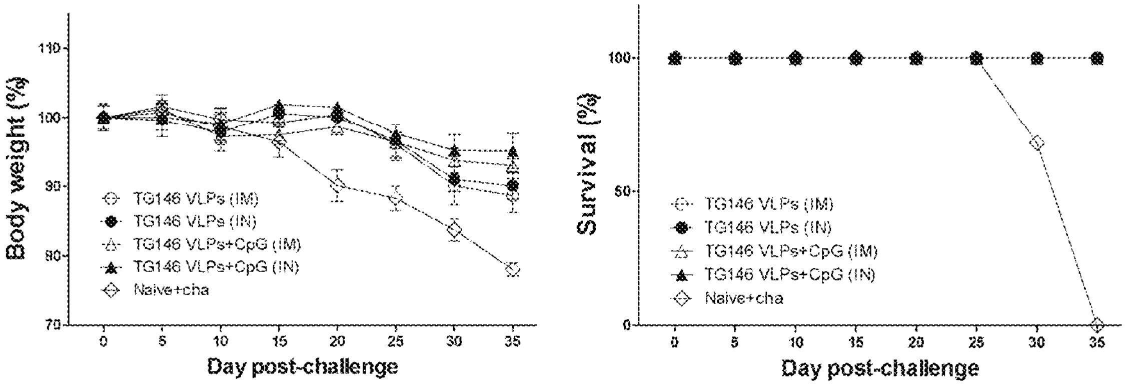
FIG. 19 shows the body weight changes and survival rates after challenge infection of each group in the double immunization animal experiment.

As a result, as shown in FIG. 19, all mice in the positive control group (Naïve+cha) died at 35 days after infection, but all mice in the IN immunization group or the IM immunization group (TG146 VLP and TG146 VLP+CpG) survived and there was little change in body weight.

3-3. Triple Immunized Animal Experiment 3-3-1. Preparation of an Animal Model

Figure 20:
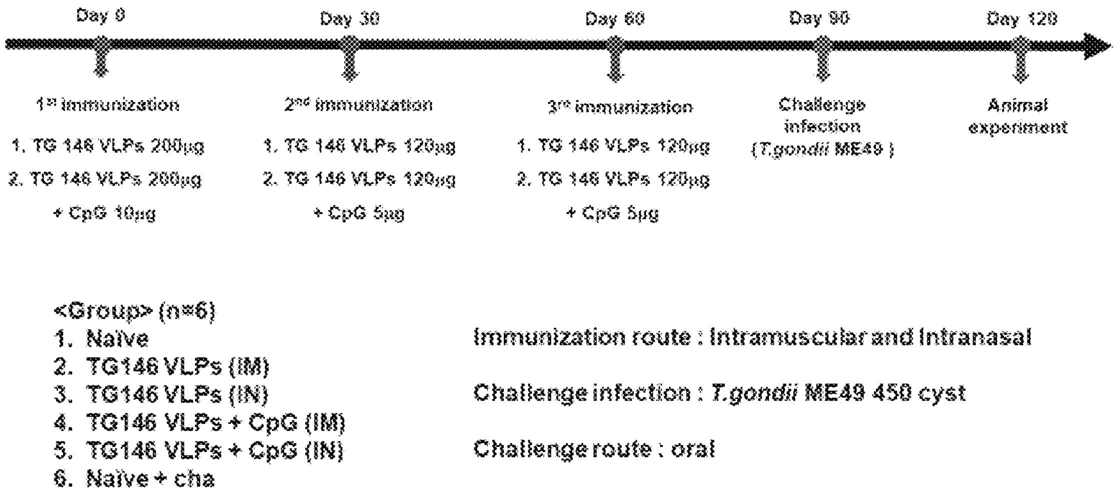
FIG. 20 shows a schematic diagram of a triple immunization animal experiment for the co-administration of *Toxoplasma gondii* VLP and CpG.

As shown in FIG. 20, mice were inoculated with 120 μg of TG146VLP or 120 μg TG146 VLP+5 μg of CpG ($2^{nd}$ immunization, Experimental Example 3-2) after inoculation of 200 μg of TG146VLP or 200 μg of TG146 VLP+10 μg of CpG by IM or IN route ($1^{st}$ immunization, Experimental Example 3-1). Then, the mice were immunized with the same amount as the $2^{nd}$ immunization at 30 days after the $2^{nd}$ immunization ($3^{rd}$ immunization). At 30 days after the $3^{rd}$ immunization, the mice were challenged with a lethal dose of *Toxoplasma gondii* ME49 450 cysts by oral route, and then sacrificed at 30 days after infection when the degree of infection maximized to isolate brain, spleen and mesenteric lymph nodes (MLN). The activity of the immune cells, the antibody response in serum, the inflammatory response in the brain, and the size and count of cysts detected in the brain were determined. Living mice in each group were monitored for body weight change and survival rate.

3-3-2. Test of *Toxoplasma gondii*-Specific Antibody Response

As in the single immunization and double immunization animal experiments, the IgG and IgA antibody responses in the sera of mice obtained 30 days after the $1^{st}$, $2^{nd}$ and $3^{rd}$ immunizations and challenge infection were determined.

Figure 21:
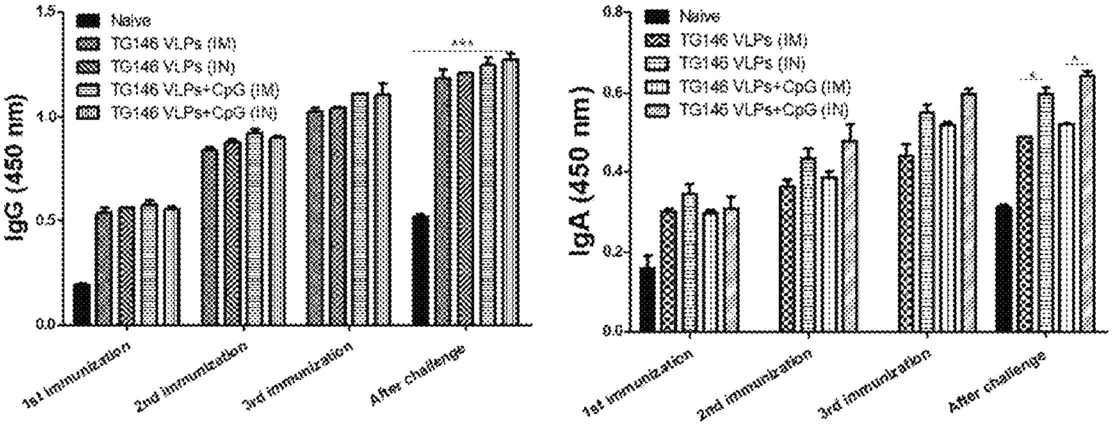
FIG. 21 shows the levels of *Toxoplasma gondii*-specific IgG and IgA in serum after $1^{st}$, $2^{nd}$ and $3^{rd}$ immunizations and challenge infection of a negative control (Naïve), a group injected with the TG146 VLP by IM route (TG146 VLPs (IM)), a group injected with the TG146 VLP by IN route (TG146 VLPs (IN)), a group injected with TG146 VLP and CpG by IM route (TG146 VLPs+CpG (IM)), and a group injected with TG146 VLP and CpG by IN route (TG146 VLPs+CpG (IN)) in the triple immunization animal experiment.

As a result, as shown in FIG. 21, the IgG antibody response level gradually increased according to the number of immunizations, and immune response was significantly higher than the positive control (Naïve+cha). In addition, the IN immunization induced higher levels of serum IgA compared to the IM immunization (* P<0.05, *** P<0.001).

3-3-3. Test of Immune Cell Response

As in the single and double immunization animal experiments, the activities of $CD4^+$ T cells, $CD8^+$ T cells, germinal center B cells and B cells in the spleen and mesenteric lymph nodes (MLN) of mice isolated at 30 days after challenge infection were analyzed.

Figure 22:
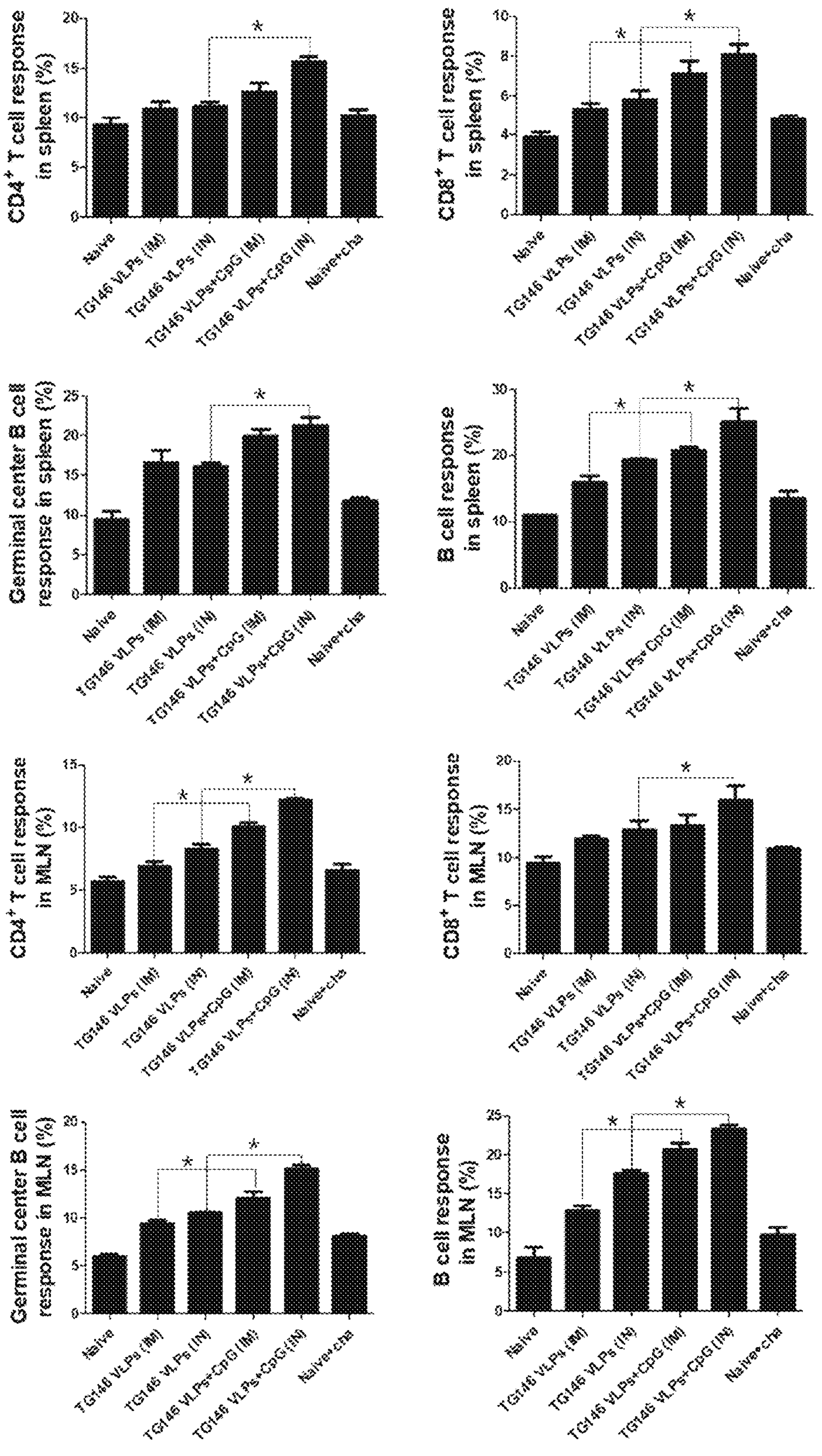
FIG. 22 shows the results of flow cytometry of the spleen and mesenteric lymph node (MLN) after challenge infection of each group in the triple immunization animal experiment.

As a result, as shown in FIG. 22, for the IN immunization, the levels of $CD4^+$ T cells, $CD8^+$ T cells, germinal center B cells and B cells in the spleen and MLN were significantly higher in the TG146 VLP+CpG group compared to the TG146 VLP group. For the IM immunization, the levels of $CD8^+$ T cells and B cells in the spleen, and the levels of $CD4^+$ T cells, germinal center B cells and B cells in MLN were significantly higher (* P<0.05). In particular, when the TG146 VLP and CpG were additionally inoculated intranasally, the best immune cell activity was shown.

3-3-4. Test of Inflammatory Response

As in the single and double immunization animal experiments, the inflammatory response was determined in the brains of mice isolated at 30 days after challenge, and the levels of inflammatory cytokines IFN-γ and IL-6, which are indicators of the inflammatory response, were analyzed and compared between groups.

Figure 23:
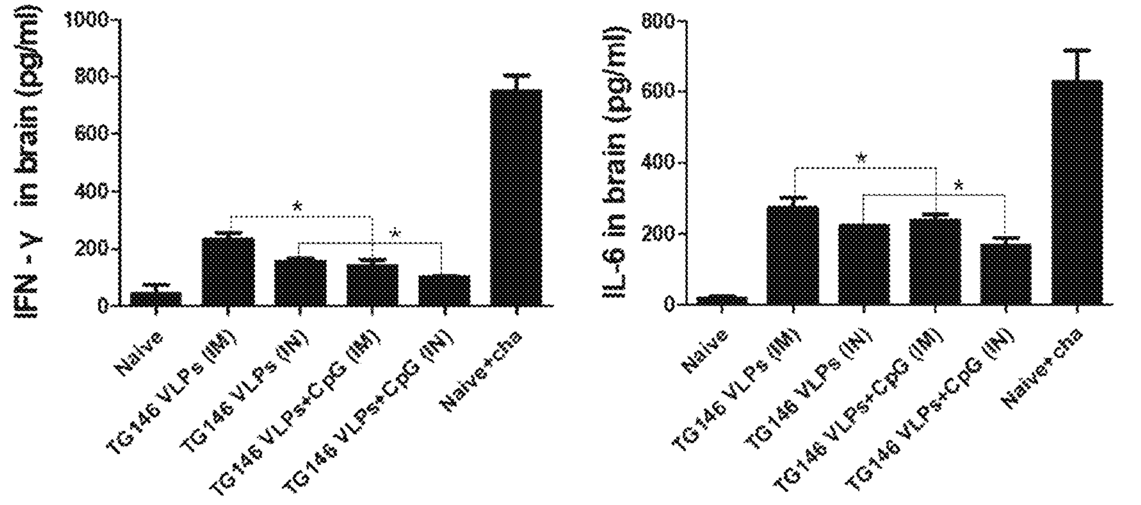
FIG. 23 shows the levels of inflammatory cytokines after challenge infection of each group in the triple immunization animal experiment.

As a result, as shown in FIG. 23, the levels of inflammatory cytokines IFN-γ and IL-6 were the highest in the positive control group (Naïve+cha), and other immunization groups (TG146 VLP and TG146 VLP+CpG) showed significantly low levels of IFN-γ and IL-6 in both the IM immunization and the IN immunization. Particularly, the group of mice further inoculated with CpG showed lower levels of IFN-γ and IL-6 (* P<0.05). In addition, when compared with the results of inflammatory response test analyzed after the $1^{st}$ and the $2^{nd}$ immunizations, markedly lowered inflammatory response was found after the $3^{rd}$ immunization (FIGS. 11, 17 and 23).

3-3-5. Test of the Size and Count of Cysts in the Brain Following Infection

As in the single and double immunization animal experiments, the size and count of cysts collected from the brains of mice isolated at 30 days after challenge was determined.

Figure 24:
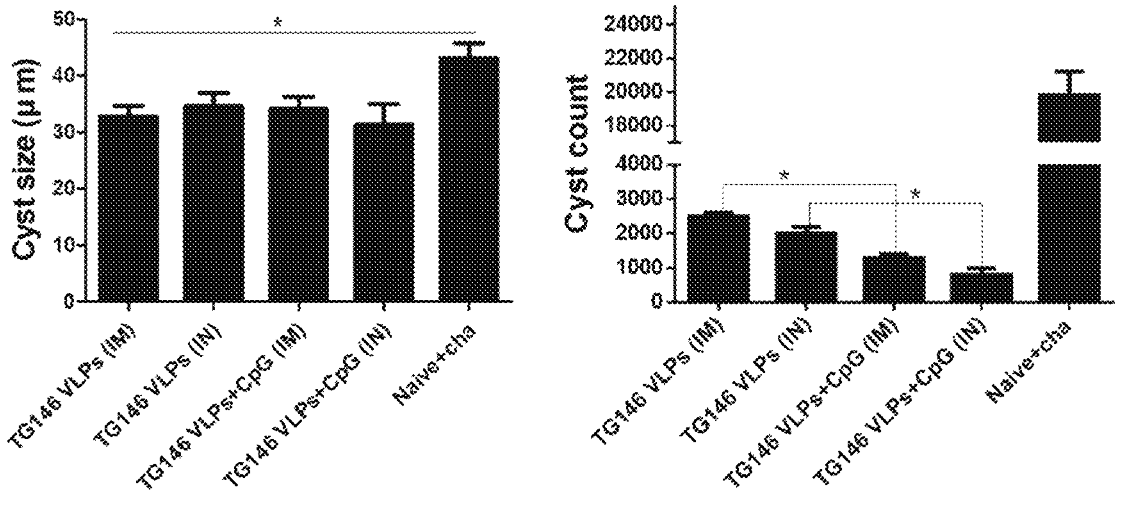
FIG. 24 shows the sizes and counts of cysts in brain tissues after challenge infection of each group in the triple immunization animal experiment.

As a result, it was found that the count of cysts was significantly decreased after the $3^{rd}$ immunization compared to the count of cysts in the brains isolated after the $1^{st}$ and the $2^{nd}$ immunizations (FIGS. 12, 18 and 24). Further, as shown in FIG. 24, the count of cysts was the lowest when immunized with TG146 VLP+CpG intranasally. The size of the cyst was also the smallest in the TG146 VLP+CpG (IN) group compared to Naïve+cha group (* P<0.05).

3-3-6. Test of Survival Rate and Body Weight Change Following Infection

As in the single and double immunization animal experiments, survival rates and body weight changes of mice in each group were determined for 35 days after challenge.

Figure 25:
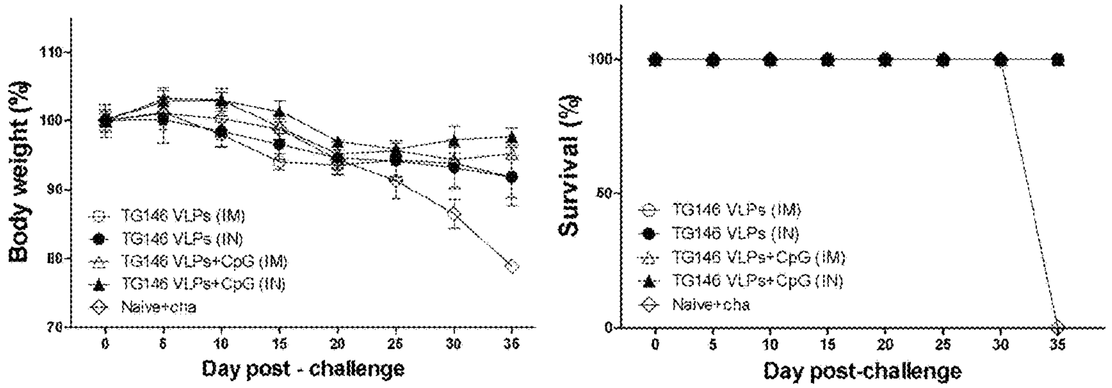
FIG. 25 shows the body weight changes and survival rates after challenge infection of each group in the triple immunization animal experiment.

As a result, as shown in FIG. 25, all mice in the positive control group (Naïve+cha) died at 35 days after infection, but all mice in the IN immunization group or the IM immunization group (TG146 VLP and TG146 VLP+CpG) survived and there was little change in body weight.

The description of the invention is for illustrative purposes, and a skilled person in the art will understand that it can be easily modified into other specific forms without changing the technical idea or essential characteristics of the present invention. Therefore, it should be understood that the examples described above are illustrative in all respects and not restrictive. For example, each component described as a single type may be implemented in a distributed manner, and similarly, components described as distributed may be implemented in a combined form.

The scope of the present invention is indicated by the following claims, and all modifications or variations derived from the meaning and scope of the claims and equivalent concepts should be construed as being included in the scope of the present invention.

What is claimed is:

1. A virus-like particle, comprising:

influenza virus matrix protein 1 (M1); and surface antigen proteins comprising an inner membrane complex (IMC), Rhoptry protein 18 (ROP18) and Microneme protein 8 (MIC8) derived from *Toxoplasma gondii*.

2. The virus-like particle of claim 1, wherein the influenza virus matrix protein 1 (M1) consists of the amino acid sequence of (SEQ ID NO: 1), the inner membrane complex (IMC) consists of the amino acid sequence of (SEQ ID NO: 2), the Rhoptry protein 18 (ROP18) consists of the amino acid sequence of (SEQ ID NO: 3), and the Microneme protein 8 (MIC8) consists of the amino acid sequence of (SEQ ID NO: 4).

3. The virus-like particle of claim 1, wherein the influenza virus matrix protein 1 (M1) is encoded by the nucleic acid sequence of (SEQ ID NO: 5), the inner membrane complex (IMC) is encoded by the nucleic acid sequence of (SEQ ID NO: 6), the Roptry protein 18 (ROP18) is encoded by the nucleic acid sequence of (SEQ ID NO: 7), and the Microneme protein 8 (MIC8) is encoded by the nucleic acid sequence of (SEQ ID NO: 8).

4. A pharmaceutical composition comprising the virus-like particle of claim 1 as an active ingredient.

5. The pharmaceutical composition of claim 4, wherein the composition is administered to a subject intranasally.

6. The pharmaceutical composition of claim 4, wherein the composition is administered in combination with cytosine-phosphorothioate-guanine (CpG).

7. The pharmaceutical composition of claim 4, wherein the composition is administered to a subject 1 to 3 times.

8. A method for preventing or treating toxoplasmosis, comprising administering the virus-like particle of claim 1 in an immunologically effective amount to a subject.

9. An expression vector for preparing a virus-like particle comprising a nucleic acid sequence of (SEQ ID NO: 5) encoding influenza virus matrix protein 1 (M1); a nucleic acid sequence of (SEQ ID NO: 6) encoding an inner membrane complex (IMC); a nucleic acid sequence of (SEQ ID NO: 7) encoding Rhoptry protein 18 (ROP18); and a nucleic acid sequence of (SEQ ID NO: 8) encoding Microneme protein 8 (MIC8).

10. The expression vector for preparing a virus-like particle of claim 9, wherein the influenza virus matrix protein 1 (M1) consists of the amino acid sequence of (SEQ ID NO: 1), the inner membrane complex (IMC) consists of the amino acid sequence of (SEQ ID NO: 2), the Rhoptry protein 18 (ROP18) consists of the amino acid sequence of (SEQ ID NO: 3), and the Microneme protein 8 (MIC8) consists of the amino acid sequence of (SEQ ID NO: 4).

11. A host cell transformed with the expression vector of claim wherein the host cell is a non-human cell.

12. The host cell of claim 11, wherein the host cell is a microorganism, an animal cell, a plant cell, a cultured cell derived from an animal, or a cultured cell derived from a plant, wherein the animal cell is a non-human cell.

13. A method for preparing a virus-like particle, comprising transforming a host cell with the expression vector of claim 9; and culturing the host cell to express the virus-like particle.

* * * * *